(12) United States Patent
Oh et al.

(10) Patent No.: US 8,846,611 B2
(45) Date of Patent: Sep. 30, 2014

(54) SKIN CONDITIONS USING HUMAN GROWTH HORMONE

(75) Inventors: Dahl Kyun Oh, Kangwon-do (KR);
Sang Jung Baik, Kangwon-do (KR);
Kyung Young Lee, Kangwon-do (KR)

(73) Assignee: Regeron, Inc., Chuncheon (KR)

( * ) Notice: Subject to any disclaimer, the term of this patent is extended or adjusted under 35 U.S.C. 154(b) by 161 days.

(21) Appl. No.: 11/279,555

(22) Filed: Apr. 12, 2006

(65) Prior Publication Data

US 2007/0081963 A1    Apr. 12, 2007

(30) Foreign Application Priority Data

Oct. 12, 2005   (WO) ................ PCT/KR2005/003402
Dec. 7, 2005    (KR) ........................ 10-2005-0119008

(51) Int. Cl.
| | |
|---|---|
| A61K 38/27 | (2006.01) |
| C07K 14/61 | (2006.01) |
| A61K 8/64 | (2006.01) |
| A61K 9/127 | (2006.01) |
| A61Q 19/00 | (2006.01) |
| A61K 8/14 | (2006.01) |
| A61Q 19/08 | (2006.01) |
| A61Q 19/02 | (2006.01) |
| A61K 9/00 | (2006.01) |
| A61Q 7/00 | (2006.01) |

(52) U.S. Cl.
CPC ... *A61K 8/14* (2013.01); *A61K 8/64* (2013.01); *A61K 9/127* (2013.01); *A61Q 19/00* (2013.01); *A61Q 19/08* (2013.01); *A61Q 19/02* (2013.01); *A61K 38/27* (2013.01); *A61K 9/0014* (2013.01); *A61Q 7/00* (2013.01)
USPC .......................................................... 514/5.1

(58) Field of Classification Search
None
See application file for complete search history.

(56) References Cited

U.S. PATENT DOCUMENTS

| | | | | | |
|---|---|---|---|---|---|
| 5,006,509 | A | * | 4/1991 | Waago | 514/12 |
| 5,077,057 | A | * | 12/1991 | Szoka, Jr. | 424/1.21 |
| 6,239,105 | B1 | * | 5/2001 | Brewitt | 514/12 |
| 6,274,582 | B1 | | 8/2001 | Mårin | |
| 6,309,381 | B1 | | 10/2001 | Castagnino | |
| 7,700,109 | B2 | | 4/2010 | Lee et al. | |
| 2002/0049422 | A1 | * | 4/2002 | Brewitt | 604/500 |
| 2002/0146379 | A1 | | 10/2002 | Shefer et al. | |
| 2004/0208902 | A1 | | 10/2004 | Gupta | |
| 2004/0253326 | A1 | * | 12/2004 | Mesko | 424/725 |

FOREIGN PATENT DOCUMENTS

| | | |
|---|---|---|
| KR | 10-2002-0032795 A | 5/2002 |
| KR | 10-2004-0027829 A | 4/2004 |
| WO | 2007-043721 A1 | 4/2007 |

OTHER PUBLICATIONS

Monafo et al. Pediatric Dermatology vol. 17, No. 3: 227-230, 2000.*
Edmondson et al. 'Interactions between growth hormone, insulin-like growth factor I, and basic fibroblast growth factor in melanocyte growth.' J Clin Endocrinol Metab 1999, vol. 84, No. 5, pp. 1638-1644.
Lantos et al. 'Ethical issues in growth hormone therapy.' JAMA 1989 vol. 261, No. 7, pp. 1020-1024.
Perls et al. 'Antiaging quackery: human growth hormone and tricks of the trade—more dangerous than ever . . . ' J Gerontol A Biol Sci Med Sci 2004 vol. 59, No. 7, pp. 682-691.
IPRP (International Preliminary Report on Patentability) for PCT/KR2005/003402 dated Apr. 16, 2008.
"Notice of Preliminary Rejection" dated Jan. 13, 2007, issued by the Korean Intellectual Property Office in connection with Republic of Korea patent application No. 10-2005-0119008.
"Notice of Allowance" dated Mar. 14, 2007, issued by the Korean Intellectual Property Office in connection with Republic of Korea patent application No. 10-2005-0119008.
Bos et al., "The 500 Dalton rule for the skin penetration of chemical compounds and drugs", Exp Dermatol 2000: 9: 165-169.
Kambayashi et al., Exp Dermatol. 2003; 12 Suppl 2:22-7.
Prausnitz et al., "Transdermal drug delivery", Nature Biotechnology, vol. 26, No. 11, Nov. 2008, 1261-1268.
Chen et al., "Transdermal protein delivery by a coadministered peptide identified via phage display", Nature Biotechnology, vol. 24, No. 4, Apr. 2006, 455-460.
Liddo et al., "Recombinant human TAT-OPI to enhance NGF neurogenic potential: preliminary studies on PC12 cells", Protein Engineering, Design & Selection, vol. 23, No. 11, pp. 889-897, 2010.
Sabatier et al., "Evidence of Neurotoxic Activity of tat from Human Immunodeficiency Virus Type 1", Journal of Virology, Feb. 1991, p. 961-967, vol. 65, No. 2.
Weeks et al., "Neurotoxicity of the Human Immunodeficiency Virus Type 1 Tat Transactivator to PC12 Cells Requires that Tat Amino Acid 49-58 Basic Domain", Journal of Neuroscience Research 42:34-40 (1995).
King et al., "HIV tat and neurotoxicity", Microbes and Infection 8 (2006) 1347-1357.
Colletier et al., "Protein encapsulation in liposomes: efficiency depends on interactions between protein and phospholipid bilayer", BMC Biotechnology 2002, 2, 1-8.

(Continued)

*Primary Examiner* — Christine J Saoud
(74) *Attorney, Agent, or Firm* — Edwards Wildman Palmer LLP; Kongsik Kim; Mark D. Russett

(57) ABSTRACT

Disclosed herein is a skin condition-improving composition for topical application to the skin, comprising human growth hormone as an active ingredient, and a method for improving skin conditions using the same. The disclosed composition exhibits various skin conditioning effects, such as acne treatment, wrinkle improvement, dark spot removal, skin elasticity improvement, hair growth stimulation, skin aging prevention, skin moisturization and the proliferation of skin epidermal stem cells.

6 Claims, 21 Drawing Sheets

(56) References Cited

OTHER PUBLICATIONS

Monafo et al., "Transient Beneficial Effect of GH Replacement Therapy and Topical GH Application on Skin Ulcers in a Boy with Prolidase Deficiency", Pediatric Dermatology, vol. 17, No. 3, pp. 327-230, 2000.

Dahlkyun Oh, "Validating Proteins as Functional Cosmetic Ingredients—an hGH Case", SOFW-Journal, 135, 5, 2009, pp. 1-11.

Chen et al., "An overview of liposome lyophilization and its future potential", Journal of Controlled Release 142(2010) 299-311.

Ahn et al., "Iontophoretic Delivery of Drugs Across the Skin", Seoul University Journal of Pharmaceutical Sciences, vol. 15, 1990, 79-99.

Kathi C Madison, "Barrier Function of the Skin: "La Raison d'Etre" of the Epidermis", Journal of Investigative Dermatology (2003) 121, 231-241.

Dae Hun Suh, MD, "Pharmacologic Treatment of Acne", J Korean Med Assoc Jul. 2010; 53(7); 623-629.

Anil M. Dwivedi, "Residual Solvent Analysis in Pharmaceuticals", Pharmaceutical Technology, Nov. 2002, 42-46.

Mansure et al., "Trehalose inhibits ethanol effects on intact yeast cells and liposomes", Biochimica et Biophysica Acta 1191(1994)309-316.

Korean Patent Court Decision in Korean Patent No. KR0912462 decided Nov. 3, 2011.

Choi et al., "Penetration of a Tat-Superoxide Dismutase Fusion Protein into Skin", The Journal of Skin Barrier Research, vol. 3, pp. 55-61 (2001).

Matsuyama et al., "Pre Symptomatic Medicine and Anti Aging", Status of Japanese Anti-aging Medical Treatments, 2003, 8, vol. 12, No. 1, pp. 23-29 (with partial English translation).

Klatz, "Grow Young with HGH", p. 36 (1998).

Rudman, et al., "Effects of Human Growth Hormone in Men Over 60 Years Old", The New England Journal of Medicine, vol. 323, No. 1, pp. 1-6 (1990).

Chein et al., "Clinical Experiences Using a Low-Dose, High-Frequency Human Growth Hormone Treatment Regimen", Journal of Advancement in Medicine, vol. 12, No. 3, pp. 183-191 (1999).

deMarco, "Anti-Aging Breakthrough: Homeopathic Growth Factor", Let's Live Magazine, Jan. 1998.

Cotsarelis G., et al., "Epithelia 1 stem cells in the skin: definition, markers, localization and functions," Experimental Dermatology, vol. 8, No. 1, pp. 80-88 (1999).

Short, S. et al., "Percutaneous Absorption of Biologically-Active Interferon-gamma in a Human Skin Graft-Nude Mouse Model", Pharm. Research, vol. 13, No. 7, pp. 1020-1027 (1996).

Niemiec, S., et al., "Influence of Nonionic Liposomal Composition on Topical Delivery of Peptide Drugs into Pilosebaceous Units: An in Vivo Study Using the Hamster Ear Model", Pharm. Research, vol. 12, No. 8, pp. 1184-1188 (1995).

Oakes, S.R. et al., "Demonstration and Localization of Growth Hormone Receptor in Human Skin and Skin Fibroblasts", Jrl. Clinical Endocrinology and Metabolism, vol. 75, No. 5, pp. 1368-1373 (1992).

Green, H. et al., "A Dual Effector Theory of Growth-Hormone Action", Differentiation, vol. 29, pp. 195-198 (1985).

Tavakkol, A. et al., "Expression of Growth Hormone Receptor, Insulin-Like Growth Factor 1 (IGF-1) and IGF-1 Receptor mRNA and Proteins in Human Skin", J. invest. Dermatol., 99(3):343-9 (1992).

deMarco M.D., C., et al., "Anti-Aging Breakthrough: Homeopathic Growth Factor", Let's Live Magazine, (Jan. 1998).

Rudman M.D., D. et al., "Effects of Human Growth Hormone in Men over 60 Years Old", The N.E. Jrl. of Medicine, vol. 323, No. 1 (1990).

Chein, M.D., E. et al., "Clinical Experiences Using a Low-Dose, High-Frequency Human Growth Hormone Treatment Regimen", Jrl. Adv. in Medicine, vol. 12, No. 3, pp. 183-191 (Fall 1999).

Robertson, J.G. et al., "Growth Hormone But Not Insulin-Like Growth Factor-I Improves Wound Strength in Pigs", Wound Repair and Regeneration, vol. 5, No. 2, pp. 168-174 (1997).

Zouboulis, C.C. et al., "Is Acne Vulgaris a Genuine inflammatory Disease?", Dermatology, vol. 203, pp. 277-279 (2001).

Kirjavainen, M. et al., "Liposome-skin interactions and their effects on the skin permeation of drugs," European Jrl. of Pharm. Sciences, vol. 7, pp. 279-286 (1999).

Loble, P.E. et al., "Localization of the growth hormone receptor/binding protein in skin", joe.endocrinology-journals.org, J. Endocrinol., 126 (Sep. 1, 1990).

Halloy, J. et al., "Modeling the dynamics of human hair cycles by a follicular automaton", PNAS, vol. 97, No. 15, pp. 8328-8333 (Jul. 18, 2000).

Alonso, L. et al., "Stem cells of the skin epithelium", PNAS, vol. 100, Suppl. 1, pp. 11830-11835 (Sep. 30, 2003).

Naik, A. et al., "Transdermal drug delivery: overcoming the skin's barrier function", PSTT, vol. 3, No. 9, pp. 318-326 (Sep. 2000).

Cevc, Gregory, "Transfersomes, Liposomes and Other Lipid Suspensions on the Skin: Permeation Enhancement, Vesicle Penetration, and Transdermal Drug Delivery", Critical Reviews in Therapeutic Drug Carrier Systems, 13 (3&4):257-388 (1996).

* cited by examiner hGH peak phospholipid peak

Stability of Nanolipo-hGH

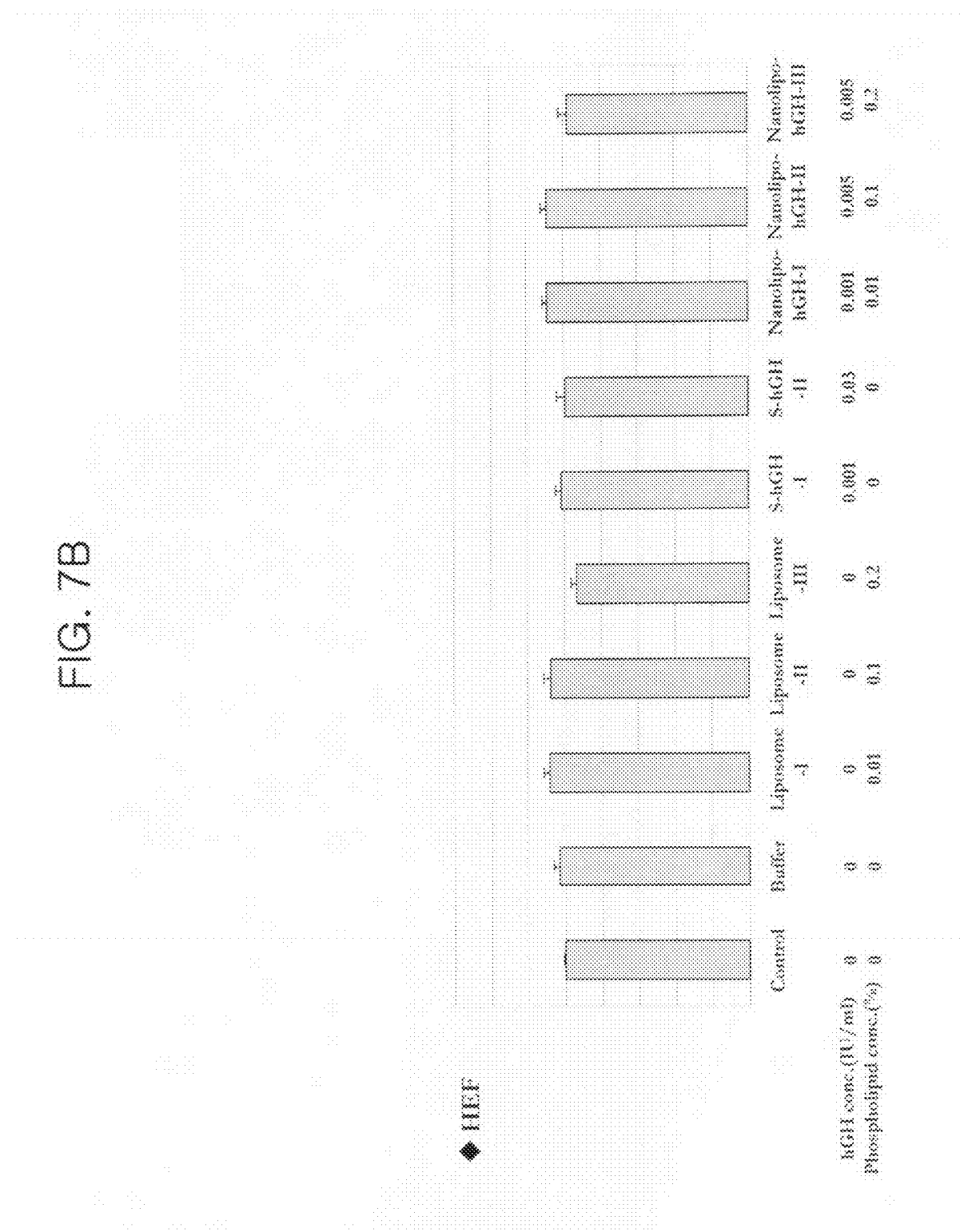

0.001 U Nanolipo-hGH treated SD rat skin (×40)

0.001 U hGH treated SD rat skin 0.001 U Nanolipo-hGH treated SD rat skin (x 40)

0.001 U Nanolipo-hGH treated SD rat skin (x 40)

Non treated ICR
mouse skin

Liposome treated ICR
mouse skin 0.1U Nanolipo-hGH treated
ICR mouse skin ( x 100)

Non treated ICR mouse skin 0.1U Nanolipo-hGH treated
ICR mouse skin ( x 400)

Liposome treated human artificial skin 0.001U Nanolipo-hGH treated human artificial skin ( x 100)

Liposome treated skin 0.01 U Lipo-hGH treated skin hGH Localization in the Hair Follicle Delivered
via Nanolipo-hGH Non treated mouse skin (X400)

hGH Localization in the Hair Follicle Delivered
via Nanolipo-hGH

Nanolipo-hGH treated mouse skin (X400)

FIG. 17A

Non treated skin (x200)

FIG. 17B

Liposome treated skin (x200)

FIG. 17C

Nanolipo-hGH treated skin (x200)

SKIN CONDITIONS USING HUMAN GROWTH HORMONE

BACKGROUND OF THE INVENTION

1. Field of the Invention

The present invention relates to skin condition-improving compositions for topical application to the skin, which comprises human growth hormone as an active ingredient and a method for improving skin conditions of a human.

2. Description of the Related Art

It is a general conception that macromolecules, especially hydrophilic proteins such as human growth hormone (molecular weight of about 22 kD), can not pass through the skin stratum corneum. A molecular weight that can be delivered efficiently and safely through the skin epidermis is generally recognized to be no more than about 500 dalton to the intact skin, or at most 2 kD even with the help of skin penetration enhancers. Accordingly, applying a protein such as human growth hormone topically to the intact skin and expecting cosmetic (for example, anti-wrinkle, etc.) or medical (for example, anti-acne, etc.) efficacies by the action of the protein have been considered non-sensible.

Some rare attempts have been made to deliver proteins to the dermal layer of the skin by topical application of liposomes encapsulating the proteins. There also have been some controversy over which routes the protein-encapsulating liposomes take to reach the dermis, one through the stratum corneum or the other through the hair follicles, when applied topically to the skin. For delivery through hair follicles, either a carrier in the form of liposomes or a lipid composite comprising lipids such as fatty acids has been reported to be favorable. In addition, although efficiencies turned out to be much lower, an aqueous solution containing an organic solvent such as ethanol, or an aqueous solution containing a polymer such as polyethylene glycol, has also been tested as a facilitating medium for delivery through hair follicles. With respect to efficiencies of delivering proteins through the skin using liposomes carrying proteins, a general principle has not been established yet, because cases of liposomal protein deliveries have been scarce and even in those rare cases, the efficiencies of protein deliveries varied widely depending on the empirical choices of the target proteins and the nature of the liposomes used. One thing to note is that, although the idea of delivering proteins through hair follicles is gaining more acceptances, even when a protein is delivered in a liposome-encapsulated form, liposomes may not pass through the infundibular portion of the hair follicles intact, rather they may undergo different morphological transformations or phase transitions owing to, first, the characteristics of the phospholipids conferring inside and outside pH's and charge valences of the liposomes, second, those of the proteins attached to or encapsulated by the liposomes, and third, those of the constituting ingredients of the surrounding tissues making up the hair follicles. Thus as a whole, these three factors and their complex interactions seem to determine follicular delivery efficiencies of the liposomes containing the proteins in question through empirical formulations rather than by a general guiding principle at the moment. What is particularly noteworthy with regard to the present invention is the existence of a report stating human growth hormone receptors are located on the living cell layers of the epidermis and throughout the ancillary organs and tissues constituting and surrounding the hair follicles.

Human growth hormone is secreted from the anterior lobe of pituitary gland and circulates with blood while it influences each organ of the human body. In the growth stage of a human, it is particularly involved in the growth of skeleton, an increase in muscles, the decomposition of fat, the growth of the internal organs, sexual growth and the like. In addition, it was suggested that when human growth hormone was administered by injection to adults at a physiological range of blood concentration, it would show various effects, such as the strengthening of the heart circulatory system, the enhancement of exercise ability, the strengthening of muscles, the reduction in abdominal fatness, the increase in libido, the improvement of improvement of arteriosclerosis, and the improvement of geriatric depression. It is known that the effects of human growth hormone on the human body are not caused by the human growth hormone itself, but rather are caused by the action of insulin-like growth factor-1 (IGF-1), the expression of which is stimulated by human growth hormone and which is produced mainly in the liver and secreted into blood. This is because the blood half-time of human growth hormone is about 15 minutes, whereas the blood half-time of IGF-1 is about 20 hours, indicating that IGF-1 can be lasting much longer than human growth hormone. Concretely speaking, human growth hormone secreted from pituitary gland binds to human growth hormone-binding protein present in blood, migrates with blood circulation, and meets a human growth hormone receptor present in each tissue of the human. At this time, the human growth hormone is liberated from the human growth hormone-binding protein while it binds to the human growth hormone receptor, and the synthesis and secretion of IGF-1 are stimulated as a result of signaling caused by the binding. The IGF-1 secreted into blood then binds to an IGF-1 binding protein, and circulates with blood flow while it binds to an IGF-1 receptor present in each tissue of the human body, thus exhibiting various physiological effects caused by the secretion of human growth hormone. Accordingly, if the effect of the injection agent human growth hormone on the skin will be actually shown, it will be an effect caused by the action of IGF-1, and thus will necessarily depend on the presence or absence of the IGF-1 receptor on the surface of dermal cells that can be brought into direct contact with blood. Even if the skin is considered to be influenced directly by human growth hormone, but not by IGF-1, the influence will necessarily be transferred by the human growth hormone receptor present at sites which are in contact with blood. Therefore, it is considered that expecting any effect on the skin by applying human growth hormone (having molecular size that cannot pass through the skin) together with cosmetics to the normal skin surface that is not brought into direct contact with blood is not common sense. The present invention is a first report that, through a method of applying human growth hormone in the form of a cosmetic preparation to the normal skin surface that is not in direct contact with blood, but not a method of transferring the effect of human growth hormone through blood, the human growth hormone can show cosmetic and medical effects on the skin, such as the improvement of acne, wrinkles, atopic skin, skin damage caused by UV light, dark spots, freckles, dry skin and oily skin, the reduction of hair follicles, and the stimulation of hair growth.

Skin tissue consists of the epidermis, the dermis and the hypodermis. The epidermis determines the properties of the skin, and is frequently susceptible to damage directly from the external environment, and thus the repair and regeneration of the epidermis are highly important. The epidermis consists of a layer of epidermal cells. The skin epidermal cells are also called "keratinocytes", because the skin epidermal cells synthesize intermediate filament protein keratin that strengthens the epidermis, during their differentiation. These cells are layered with differentiation while migrating toward the epidermis, and become flat while organs inside the cells gradually disappear and they become dead cells. A cell layer located at the innermost portion of the epidermis is contiguous to the basal lamina and called the "stratum basale", and the cells forming the layer are called "basal cells", among which epidermal stem cells are present. The cells of the stratum basale differentiate into the epidermis while they sequentially form the stratum spinosum, the stratum granulosum, the stratum lucidum and the stratum corneum, the stratums being divided into a living cell layer at the lower position with respect to the stratum granulosum, and a dead cell layer at the upper position. Flattened scale-like tissues outside the stratum corneum are also called "squames" where keratins are densely filled. Cells located from the outside of the stratum granulosum to the stratum corneum are reinforced with a layer of cross-linked protein whose plasma membrane is thin and tough. While the epidermal cells are proliferated from the epidermal stem cells and differentiated into the stratum corneum, they are internally reinforced by the cross-linking of keratins and are also linked by keratins with desmosomes firmly linked with other cells in the same layer so as to maintain the entire layer structure thereof. The epidermal cells are differentiated into the outer epidermis while they produce and secrete lipid so as to form double-layered tissue on a plasma membrane cornified with protein, thus preventing the skin surface from the external environment, like saran wrap. Since the human epidermis is replaced at two-week interval, the proliferation ability of skin stem cells forming the epidermis can be considered to be huge.

It was recently reported that the multipotent stem cells of the skin are located at the bulge region, which lies just below the sebaceous gland of hair follicles. These bulge stem cells serve as the basis for making epidermal stem cells, hair matrix stem cells, and sebaceous glands stem cells. The bulge stem cells are located only in the bulge region and express a special combination of protein while maintaining their property as stem cells. The epidermal stem cells maintain the epidermis while they proliferate and differentiate. When a hair falls out, the hair matrix stem cells will proliferate and differentiate to make a new hair. However, the epidermal stem cells, the hair matrix stem cells or the sebaceous glands stem cells have limitations in their proliferation ability or the ability to maintain the ability of stem cells, and thus, for example, most of the epidermal stem cells will differentiate after they proliferate 3-6 times. On the other hand, although the bulge stem cells proliferate slower than the other three stem cells, it seems that the bulge stem cells can indefinitely proliferate during the life of human beings while making the epidermal stem cells, the hair matrix stem cells and the sebaceous glands stem cells and, at the same time, maintaining their stem cell character. The fact that the location of expression and action of human growth hormone is the location of the bulge stem cells has been disclosed for the first time through the present invention, and this disclosure is quite significant considering that the human growth hormone has the effect of improving various skin conditions as described in the present invention.

SUMMARY OF THE INVENTION

The present inventors have conducted studies and efforts to develop a substance capable of improving skin conditions, and as a result, found that the topical application of human growth hormone to the skin can greatly improve skin conditions, thereby completing the present invention.

Accordingly, it is an object of the present invention to provide a skin condition-improving composition for topical application to the skin.

Another object of the present invention is to provide a method for improving skin conditions.

Other objects and advantages of the present invention will become apparent from the detailed description to follow taken in conjugation with the appended claims.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 17A is a photograph showing skin not treated. FIG. 17B is a photograph showing skin treated with liposome. FIG. 17C is a photograph showing skin treated with Nanolipo-hGH of this invention.

DETAILED DESCRIPTION OF THIS INVENTION

Figure 1:
FIG. 1 is an electron microscope photograph of a human growth hormone (hGH)-containing liposome cream formulation (formulation A) prepared in Example I.

In one aspect of this invention, there is provided a composition formulated for topical administration to skin for improving skin conditions, which comprises the effective amount of human growth hormone as an active ingredient.

In another aspect of this invention, there is provided a method for improving skin conditions of a human, which comprises topically administering to the skin of human a composition comprising the effective amount of human growth hormone as an active ingredient.

The present inventors have conducted studies and efforts to find a novel use of human growth hormone and, as a result, found that the topical application of human growth hormone to the skin can greatly improve skin conditions. Current therapy with human growth hormone is performed mainly to treat dwarfism and human growth hormone deficiency using an injection method. In the prior art, because of the high molecular weight of human growth hormone and a prejudice for the action pathway of human growth hormone, it was not noticed that the topical application of human growth hormone to the normal skin makes it possible to expect the effect thereof. The present invention greatly deviates from this conventional common sense or knowledge in the art and is characterized in that the effect of the topical application of human growth hormone to the normal skin has been found for the first time. The present invention is the first invention of applying human growth hormone to the skin through two routes, i.e., hair follicles and the epidermis.

The present invention is the first report showing that, by a method of applying human growth hormone to the normal skin surface opposite to a region that is in contact with blood, but not by a method of transferring the effect of human growth hormone through blood, human growth hormone can show cosmetic and medical effects on the skin, such as the improvement of acne, wrinkles, atopic skin, skin damage caused by UV light, dark spots, freckles, dry skin and oily skin, the reduction of hair follicles, and the stimulation of hair growth.

Human growth hormone (hGH) which is used as an active ingredient in the present invention may be any polypeptide showing human growth hormone activity. For example, any one selected from the group consisting of mature hGH, Met-hGH, hGH variants, modified-hGH, hGH fragments and hGH analogues may be used. Preferred is mature hGH or Met-hGH. The mature hGH refers to a human growth hormone having the amino acid sequence of the major human growth hormone present in human blood, the Met-hGH refers to a human growth hormone having methionine added to the N-terminus of mature hGH, the hGH variants refer to human growth hormones having the amino acid sequences of human growth hormones other than the major human growth hormone present in the human body, the modified hGH refers to a human growth hormone modified by adhesion of an additive such as pegylation or glycation to at least one amino acid residue of human growth hormone, the hGH fragments indicate human growth hormones obtained by deleting a portion of the amino acid sequences of human growth hormones by a genetic engineering method or biochemical method, and the hGH analogue refers to a human growth hormone obtained by modifying the amino acid sequence of human growth hormone into another amino acid sequence having properties similar thereto by a genetic engineering method. As used herein, the phrase "having human growth hormone activity" can be specified according to one of the following two methods. In one method, it can be specified according to whether human growth hormone causes signaling by binding to a human growth hormone-binding protein or a human growth hormone receptor, and in another method, it can be specified according to whether biological effects caused by the action of human growth hormone are shown.

In the present invention, human growth hormone can be applied to the skin as an aqueous solution or with a carrier. One of the surprising characteristics of the present invention is that, as illustrated in Example XII and FIG. 10, even when an aqueous solution of human growth hormone itself is applied directly to the skin, the desired effect of improving skin conditions can be somewhat achieved. Even when an aqueous solution of human growth hormone itself is topically applied to the skin, the human growth hormone will reach the location of bulge stem cells in hair follicles and can provide the effect of improving skin conditions.

According to a preferred embodiment of the present invention, a composition according to the present invention has a phospholipid or liposome composition, and preferably a liposome composition. It is preferable that human growth hormone as an active ingredient be encapsulated in liposome and applied to the skin. According to a more preferred embodiment of the present invention, the inventive composition has a nanoliposome composition. As used herein, the term "nanoliposome" refers to a liposome having the form of conventional liposome and a mean particle diameter of 20-1000 nm. According to a preferred embodiment of the present invention, the mean particle diameter of the nanoliposome is 50-500 nm, more preferably 50-350 nm, and most preferably 50-250 nm.

Liposome is defined as a spherical phospholipid vesicle of colloidal particles which are associated with themselves, and liposomes composed of amphiphilic molecules each having a water soluble head (hydrophilic group) and a water insoluble tail (hydrophobic group) show a structure aligned by spontaneous binding caused by the interaction therebetween, and are classified, according to the size and lamellarity thereof, into SUV (small unilamellar vesicle), LUV (large unilamellar vesicle) and MLV (multi lamellar vesicle). The liposomes showing various lamellarities as described above have a double membrane structure similar to the cell membrane.

The (nano)liposome in the present invention can be prepared using phospholipid, polyol, a surfactant, fatty acid, salt and/or water.

Phospholipid which is a component used in the preparation of the inventive (nano)liposome is used as biphilic lipid, and examples thereof include natural phospholipids (e.g., egg yolk lecithin, soybean lecithin, and sphingomyelin) and synthetic phospholipids (e.g., dipalmitoylphosphatidylcholine or hydrogenated lecithin), the lecithin being preferred. More preferably, the lecithin is a naturally derived unsaturated or saturated lecithin extracted from soybean or egg yolk.

Polyols which can be used in the preparation of the inventive (nano)liposome are not specifically limited and preferably include propylene glycol, dipropylene glycol, 1,3-butylene glycol, glycerin, methylpropanediol, isoprene glycol, pentylene glycol, erythritol, xylitol and sorbitol.

The surfactant which can be used in the preparation of the inventive (nano)liposome may be any surfactant known in the art, and examples thereof include anionic surfactants (e.g., alkyl acyl glutamate, alkyl phosphate, alkyl lactate, dialkyl phosphate and trialkyl phosphate), cationic surfactants, amphoteric surfactants and nonionic surfactants (e.g., alkoxylated alkylether, alkoxylated alkylester, alkylpolyglycoside, polyglycerylester and sugar ester).

The fatty acids which can be used in the preparation of the inventive (nano)liposome are higher fatty acids, and preferably saturated or unsaturated fatty acid having a $C_{12-22}$ alkyl chain, and examples thereof include lauric acid, myristic acid, palmitic acid, stearic acid, oleic acid and linoleic acid.

The salt which is used in the preparation of the inventive (nano)liposome may be any salt known in the art, and examples thereof include phosphate salt, sulfate salt, nitrate salt, chloride salt, hydroxide salt, sodium salt, potassium salt, calcium salt, ammonium salt, amino acid salt, and amino acid.

Water which is used in the preparation of the inventive (nano)liposome is generally deionized distilled water.

According to a preferred embodiment of the present invention, the inventive (nano)liposome is prepared only with phospholipid, salt and water, as described in detail in Examples below.

According to a preferred embodiment of the present invention, the inventive hGH-containing nanoliposome is prepared through a process comprising the steps of: (a) dissolving a phospholipid capable of forming liposome (preferably, yellow yolk lecithin or soybean lecithin) in a buffered aqueous solution of salt containing human growth hormone; and (b) passing the aqueous solution containing human growth hormone and phospholipid through a high-pressure homogenizer while gradually increasing the content of the phospholipid and the pressure of the high-pressure homogenizer as the number of the passages increases, thus preparing a human growth hormone-containing nanoliposome.

The aqueous solution containing human growth hormone is preferably a buffer solution having a pH of 6-8, and more preferably about 7, for example, sodium phosphate buffer solution. If the sodium phosphate buffer solution is used, the concentration thereof will preferably be 5-100 mM, more preferably 5-60 mM, even more preferably 10-30 mM, and most preferably about 20 mM.

The most special aspect of the inventive process is that the mixture of the phospholipid and the hGH-containing aqueous solution is passed through the high-pressure homogenizer several times, in which the amount of the phospholipid and the pressure of the homogenizer are gradually increased as the number of the passages increases. According to a preferred embodiment of the present invention, the pressure of the homogenizer is gradually to 0-1000 bar, and preferably 0-800 bar. The pressure can be increased by 50 bar or 100 bar, and preferably 100 bar. According to a preferred embodiment of the present invention, the amount of the phospholipid is gradually increased to 5-40 w/v(%), and more preferably 5-30 w/v(%).

Through the high-pressure homogenization process including these gradual increases in phospholipid content and pressure, an hGH-containing nanoliposome is prepared and a liquid hGH-containing nanoliposome is preferably prepared.

The composition of the present invention is useful in the improvement in various skin conditions. Preferably, the present composition is effective in the improvement in skin conditions including acne, wrinkle, dark spots, skin elasticity, hair growth, skin aging, skin moisture and proliferation of dermal stem cell. More specifically, the improvements in skin conditions refer to the treatment of acne, improvement of wrinkle, removal of dark spots, improvement of skin elasticity, promotion of hair growth, prevention of skin aging, improvement of moisture-retaining property of skin or promotion of dermal stem cell proliferation. More preferably, the skin condition improved by the present invention is acne, wrinkle or hair growth.

The term "the effective amount" as used herein means an amount sufficient to achieve the improvement effects in the skin conditions described above.

The present composition may be provided as a cosmetic or pharmaceutical composition.

The cosmetic compositions of this invention for improving skin conditions may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these substances. In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances. The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum metahydroxide, bentonite, agar and tragacanth or mixtures of these substances.

The formulation of soap may comprise alkali metal salts of fatty acids, salts of fatty acid hemiesters, fatty acid protein hydrolyzates, isethionates, lanolin, fatty alcohol, vegetable oil, glycerol, sugars or mixtures of these substances.

Furthermore, the cosmetic compositions of this invention may contain auxiliaries as well as carrier. The non-limiting examples of auxiliaries include preservatives, antioxidants, stabilizers, solubilizers, vitamins, colorants, odor improvers or mixtures of these substances.

Where the present composition is formulated to provide a pharmaceutical composition, it may comprise a pharmaceutically acceptable carrier including carbohydrates (e.g., lactose, amylose, dextrose, sucrose, sorbitol, mannitol, starch, cellulose), gum acacia, calcium phosphate, alginate, gelatin, calcium silicate, microcrystalline cellulose, polyvinylpyrrolidone, water, salt solutions, alcohols, gum arabic, syrup, vegetable oils (e.g., corn oil, cotton-seed oil, peanut oil, olive oil, coconut oil), polyethylene glycols, methyl cellulose, methylhydroxy benzoate, propylhydroxy benzoate, talc, magnesium stearate and mineral oil, but not limited to. The pharmaceutical compositions of this invention, further may contain wetting agent, sweetening agent, emulsifier, buffer, suspending agent, preservatives, flavors, perfumes, lubricant, stabilizer, or mixtures of these substances. Details of suitable pharmaceutically acceptable carriers and formulations can be found in Remington's Pharmaceutical Sciences (19th ed., 1995), which is incorporated herein by reference.

The pharmaceutical composition of this invention is developed for topical application onto skin.

The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions. According to a preferred embodiment of this invention, the suitable dosage unit is to administer once a day with 0.001-100 ng/cm$^2$ (unit surface area of skin), most preferably, 0.1-2 ng/cm$^2$.

According to the conventional techniques known to those skilled in the art, the pharmaceutical compositions of this invention can be formulated with pharmaceutical acceptable carrier and/or vehicle as described above, finally providing several forms including a unit dosage form. Most preferably, the pharmaceutical composition is a solution comprising nanoliposomes.

The inventive composition acts on epidermal stem cell to increase the number of hair follicles so as to stimulate of hair growth, proliferates the keratinocytes of the epidermal layer to greatly inhibit skin aging, improves the skin damaged by UV light and wrinkles formed by UV light, remodel the connective tissue of the dermal layer to improve skin firmness and improve wrinkles, and shows the effects of treating acne and removing dark spots. Synthetically, the inventive composition can greatly improve skin conditions. In addition, the inventive composition is very safe to the human body, and has excellent stability when it is prepared in the form of a nano-liposome.

The following specific examples are intended to be illustrative of the invention and should not be construed as limiting the scope of the invention as defined by appended claims.

EXAMPLES

Example I

Preparation of Various Human Growth Hormone-Containing Liposome (Nanolipo-hGH) Formulations Formulation A (Cream Formulation): Human Growth Hormone-Containing Cream Formulation Phospholipid used in formulation A was lipoid S100 (Lipoid GmbH, Germany) or lipoid S75 (Lipoid GmbH, Germany).

The heat exchanger of a high-pressure homogenizer (max. output 5 L/hr, highest pressure 1200 bar, Model HS-1002; manufactured by Hwasung Machinery Co., Ltd., South Korea) was placed in ice water such that the temperature of the outlet of the homogenizer did not exceed 30° C., and the inside of the homogenizer was then washed with distilled water so as to be ready to operate. Then, to 100 ml of a solution of human growth hormone (LG Life Sciences, Ltd) dissolved in a buffer solution (20 mM NaH$_2$PO$_4$ pH 6.5-7.5, 1 mM EDTA) at a concentration of 1 mg/ml, phospholipid was added at a ratio of 5 w/v % and sufficiently hydrated and stirred. The stirred solution was passed through the homogenizer three times or more at room temperature and a low pressure of 0 bar. To the solution passed through the homogenizer, phospholipid was added to a ratio of 6 w/v % and sufficiently hydrated and stirred. The stirred solution was passed through the homogenizer three times or more at 100 bar. Then, to the solution passed through the homogenizer in the condition of 100 bar, phospholipid was added to a ratio of 7 w/v %, sufficiently hydrated and stirred, and passed through the homogenizer three times or more at 200 bar. Then, to the solution passed through the homogenizer in the condition of 200 bar, phospholipid was added to a ratio of 8 w/v %, sufficiently hydrated and stirred, and passed through the homogenizer three times or more at 300 bar. To the solution passed through the homogenizer in the condition of 300 bar, phospholipid was added to a ratio of 9 w/v %, sufficiently hydrated and stirred, and passed through the homogenizer three times or more at 400 bar. Then, to the solution passed through the homogenizer in the condition of 400 bar, phospholipid was added to a ratio of 10 w/v %, sufficiently hydrated and stirred, and passed through the homogenizer three times or more at 500 bar. Then, to the solution passed through the homogenizer in the condition of 500 bar, phospholipid was added to a ratio of 11 w/v %, sufficiently hydrated and stirred, and passed through the homogenizer thre times or more at 600 bar. Then, to the solution solution passed through the homogenizer in the condition of 600 bar, phospholipid was added to a ratio of 12 w/v %, sufficiently hydrated and stirred, and passed through the homogenizer three times or more at 800 bar, thus preparing a human growth hormone-containing liposome (Nanolipo-hGH) cream formulation.

FIG. 1 shows an electron microscope photograph of the human growth hormone-containing liposome cream formulation prepared in this Example. The liposome cream formulation prepared in this Example was coated with gold and observed with a scanning electron microscope (HITACHI S 2500). In the observation result, the shape of the bent and connected background was presumed as gel, and small spherical grains were estimated as nanosize (0.02-0.3 μm) loposomes.

Formulation B (Liposome Formulation): Human Growth Hormone (hGH)-Containing Liposome Formulation Phospholipid used in the preparation of formulation B was soybean lecithin (ShinDongBang Corp., South Korea), Metarin P (Degussa Texturant Systems Deutschland GmbH & Co. KG), Nutripur S (Degussa Texturant Systems Deutschland GmbH & Co. KG) or Emultop (Degussa Texturant Systems Deutschland GmbH & Co. KG).

Figure 2:
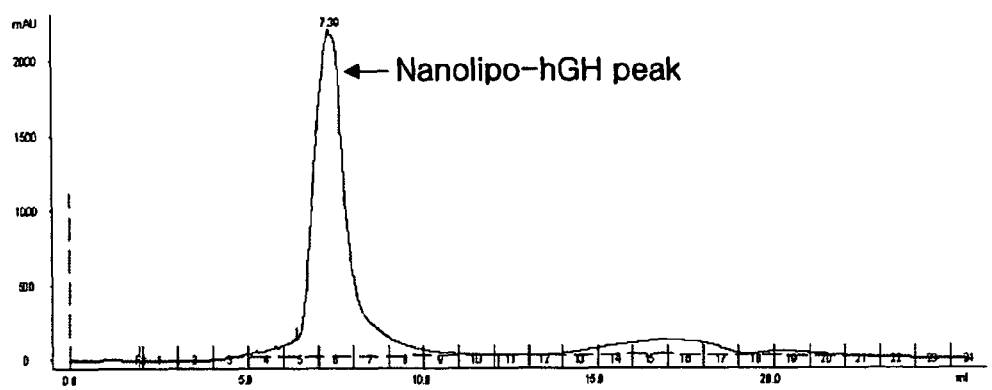
FIG. 2 is a gel permeation chromatogram of an hGH-containing liposome (Nanolipo-hGH) of formulation B prepared in Example I.

The heat exchanger of a high-pressure homogenizer (max. output 5 L/hr, highest pressure 1200 bar, Model HS-1002; manufactured by Hwasung Machinery Co., Ltd., South Korea) was placed in ice water such that the temperature of the outlet of the homogenizer did not exceed 30° C., and the inside of the homogenizer was then washed with distilled water so as to be ready to operate. Then, to 100 ml of a solution of human growth hormone (LG Life Sciences, Ltd.) dissolved in a buffer solution (20 mM NaH$_2$PO$_4$ pH 6.5-7.5, 1 mM EDTA) at a concentration of 1 mg/ml, phospholipid was added at a ratio of 10 w/v % and sufficiently hydrated and stirred. The stirred solution was passed through the homogenizer three times or more at room temperature and a low pressure of 0 bar. Then, to the solution passed through the homogenizer, phospholipid was added to a ratio of 14 w/v %, sufficiently hydrated and stirred, and passed through the homogenizer three times or more at 100 bar. Then, to the solution passed through the homogenizer, phospholipid was added to a ratio of 18 w/v %, sufficiently hydrated and stirred, and passed through the homogenizer three times or more at 200 bar. Then, to the solution passed through the homogenizer, phospholipid was added to a ratio of 20 w/v %, sufficiently hydrated and stirred, and passed through the homogenizer three times or more at 300 bar. Then, to the solution passed through the homogenizer, phospholipid was added to a ratio of 22 w/v %, and sufficiently hydrated and stirred, and passed through the homogenizer three times or more at 400 bar. Then, to the solution passed through the homogenizer, phospholipid was added to a ratio of 24 w/v %, sufficiently hydrated and stirred, and passed through the homogenizer three times or more at 500 bar. Then, to the solution passed through the homogenizer, phospholipid was added to a ratio of 26 w/v %, sufficiently hydrated and stirred, and passed through the homogenizer three times or more at 600 bar. Then, to the solution passed through the homogenizer, phospholipid was added to a ratio of 28 w/v %, sufficiently hydrated and stirred, and passed through the homogenizer three times or more at 700 bar. Then, the solution passed through the homogenizer at 700 bar was passed through the homogenizer three times or more at 800 bar and discharged from the homogenizer. The discharged solution was subjected to high-speed centrifugation at 15,000×g for 30 minutes, and the supernatant was separated. At this time, human growth hormone which has not been encapsulated in liposome was removed by gel permeation chromatography (GE Healthcare, USA), thus obtaining liquid phase liposome (see FIG. 2).

Formulation B prepared using a solution of distilled water and buffer solution (20 mM $NaH_2PO_4$, 1 mM EDTA, pH 6.0-7.5) did not show a difference in the physical properties and stability of liposome. Also, the obtained formulation was stored in more than 10 w/v % of soybean lecithin at 15-30° C. for a long period of time and, as a result, the phase separation into a lipid layer (lower) and an aqueous solution (upper) occurred. However, in less than 10 w/v % of soybean lecithin, it had excellent stability without phase separation.

Example II

FPLC Separation and SDS-PAGE Analysis

Figure 3:
FIG. 3 shows the results of SDS-PAGE for hGH encapsulated with Nanolipo-hGH of formulation B prepared in Example I.

For the analysis of the human growth hormone-containing liposome of formulation B prepared in Example I, FPLC (Acta explorer, Amersham Bioscience) was equipped with a superdex 200 HR/30 column at room temperature, and the column was equilibrated with two times the column volume of a buffer solution (20 mM $NaH_2PO_4$, 1 mM EDTA and 150 mM NaCl). Then, the human growth hormone-containing liposome was separated into fractions which were then collected and analyzed by SDS-PAGE. As shown in FIG. 3, the band of human growth hormone could be observed at about 22 kDa.

Example III

Quantification of Human Growth Hormone in Liposome

Figure 4:
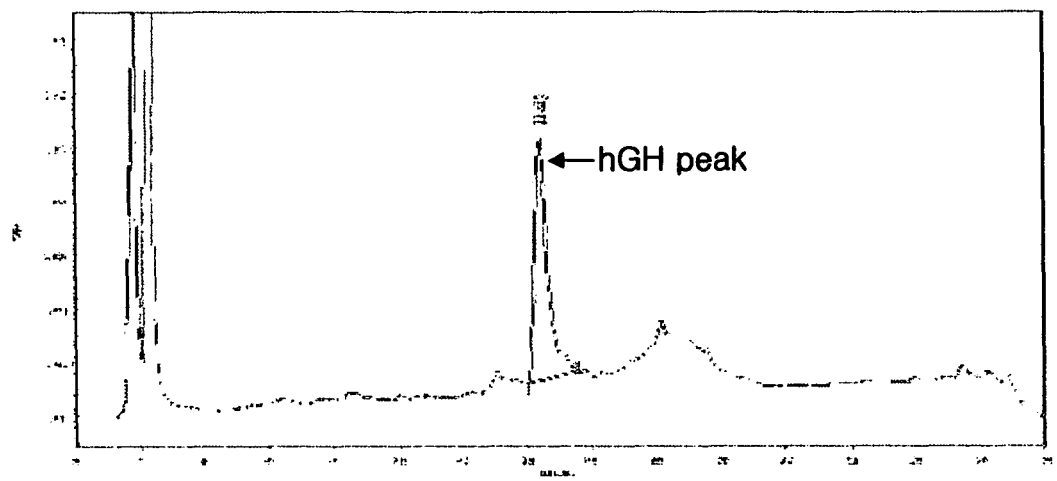
FIG. 4 is a reverse-phase HPLC chromatogram of hGH encapsulated in Nanolipo-hGH of formulation B prepared in Example I.

HPLC (Shimazu) was equipped with a $C_{18}$ Delta pack column (Waters, USA), and reverse phase-HPLC was performed by concentration gradient (B 60-10%: 0-25 min, B 60%:25.01-30 min) at a flow rate of 1 ml/min using 0.1% TFA acetonitrile as solvent A and 0.1% TFA $H_2O$ as solvent B. A standard sample (international standard human growth hormone NIBSC code 98/574) was quantified using a fluorescence detector (excitation: 295 nm, range: 270-300 nm; emission: 350 nm, range: 300-400 nm) in conditions of oven temperature of 55° C. and run time of 30 min. Then, a sample was pretreated by disrupting the human growth hormone-containing liposome solution with a sonicator and adding a buffer solution (50 mM Tris-Cl pH 8.0, 1 mM EDTA, 8 M urea, 2% Tween 20) thereto in the same volume as the sample and then pipetting the mixture, and was quantified by HPLC using the fluorescence detector (see FIG. 4).

From the quantification results, it can be seen that the Nanolipo-hGH of formulation B prepared in Example I contained about 3.69 μg/ml of human growth hormone.

Example IV

Analysis of Phospholipid Content

Figure 5:
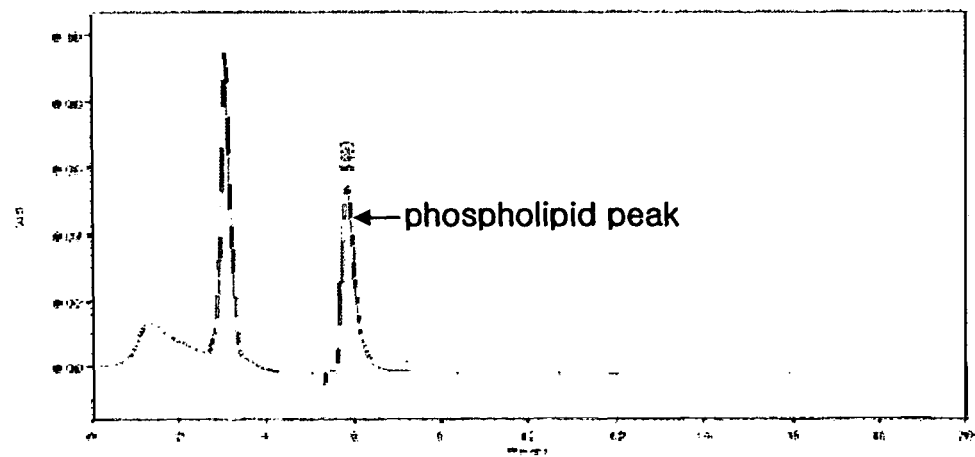
FIG. 5 is a reverse-phase HPLC chromatogram of phospholipid in Nanolipo-hGH of formulation B prepared in Example I.

HPLC (Shimazu) was equipped with a Spherisorb S5 $NH_2$ column (Waters), and HPLC was performed by isocratic gradient at a flow rate of 1 ml/min using a mixed solvent of 60% acetonitrile, 30% methanol and 5% $H_2O$. Phospholipid was completely dissolved in a mixed solvent of methanol:chloroform (90%:10%) and quantified using a UV light detector (215 nm) in conditions of oven temperature of 35° C. and run time of 20 min. In the same manner, the inventive human growth hormone-containing liposome solution was completely dissolved in a mixed solvent of methanol:chloroform (90%:10%) and then quantified by HPLC (see FIG. 5).

From the quantification results, it can be seen that the Nanolipo-hGH of formulation B prepared in Example I contained about 3.26 mg/ml of phospholipid.

Example V

Stability Test

Figure 6:
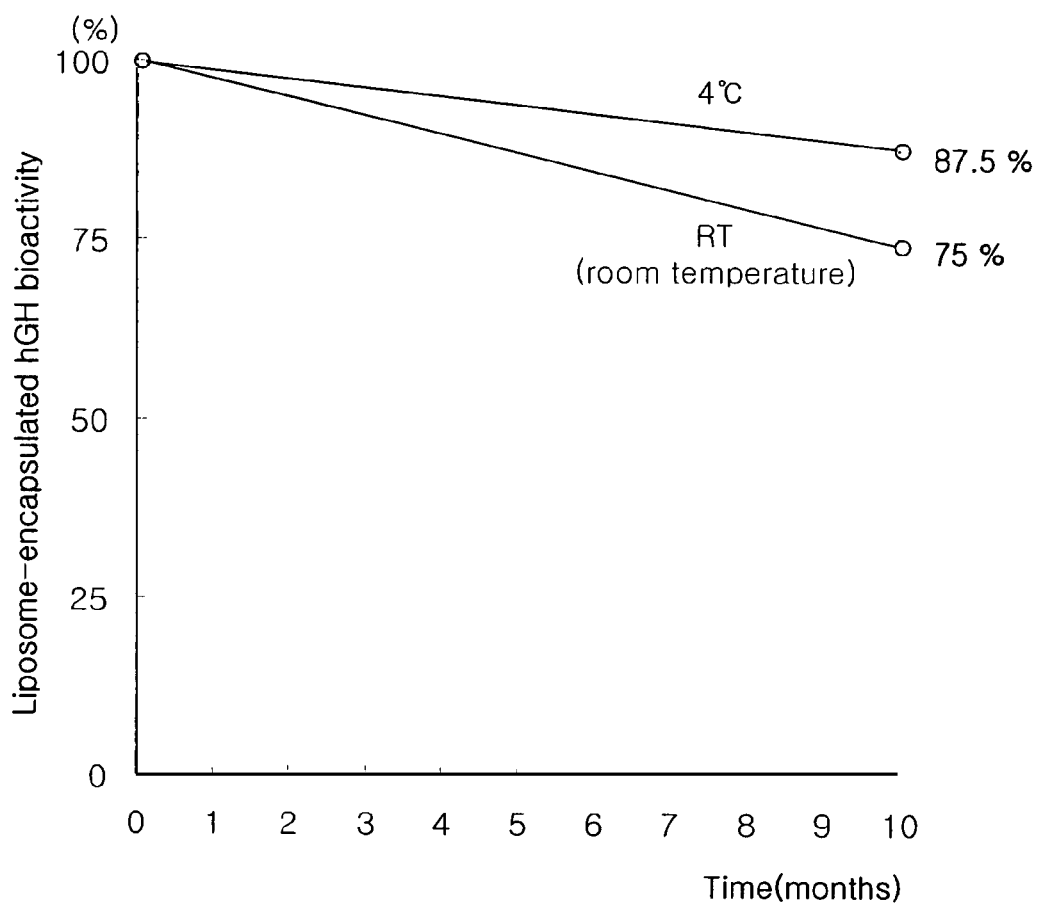
FIG. 6 is a graphic diagram showing safety test results for Nanolipo-hGH of formulation B prepared in Example I.

A stability test for the human growth hormone-containing liposome of formulation B prepared in Example I was performed in the following manner. The inventive Nanolipo-hGH containing 0.1% methyl paraben was analyzed for stability by placing it in brown color bottles, standing the bottles at 4 C.° and 15-30 C.°, respectively, and quantifying the content of hGH by HPLC at one-week intervals. As can be seen in FIG. 6, the inventive Nanolipo-hGH after 10 months of storing had initial hGH contents of 87.5% at 4 C.° and 75% at room temperature. This suggests that the inventive Nanolipo-hGH has excellent stability.

Example VI

Safety Test

To test the safety of the inventive human growth hormone-containing liposome (formulation B prepared in Example I), cytotoxicities for human keratinocyte cell line HaCaT (DKFZ, Germany) and human embryonic fibroblast HEF (gift from Prof. Lee, Jaeyong, Department of Biochemistry, School of Medicine, Hallym University) were examined.

HaCaT and HEF were suspended in 10% FBS/DMEM (FD media at concentrations of $1\times10^5$ cells/ml and $5\times10^4$ cells/ml, respectively. 1 ml of each of the suspensions was added to a 24-well plate and then cultured in a 5% $CO_2$ incubator at 37°

C. for one day. After one day of the culture, the upper-layer medium was carefully removed, and a suitable amount of 10% FD medium and various concentrations of samples were added to the wells of the plate and allowed to react in a 5% $CO_2$ incubator at 37° C. for one day. The samples used were a buffer solution (containing 20 mM Na—Pi, pH 7.0, 1 mM EDTA and 0.1% methyl paraben), liposome, human growth hormone and the Nanolipo-hGH of formulation B prepared in Example I. After the reaction, the viability of the cells was measured using 3-(4,5-dimethylthiazol-2-yl)-2,5-diphenyltetrazolium bromide (MU: Sigma, USA) (Shearman et al., Proc. Natl. Acad. Sci. 91(4): 1470-4 (1994), Shearman et al., J. Neurochem. 65(1): 218-27 (1995) and Kaneko et al., J. Neurochem. 65(6): 2585-93 (1995)). The MU reaction products were measured for absorbance at 570 nm using an ELISA reader (Molecular Devices, USA). The cell viability by each of the samples was expressed as a value relative to the absorbance of a well not containing the samples, taken as 100% (FIG. 7A, FIG. 7B).

Figure 7A:
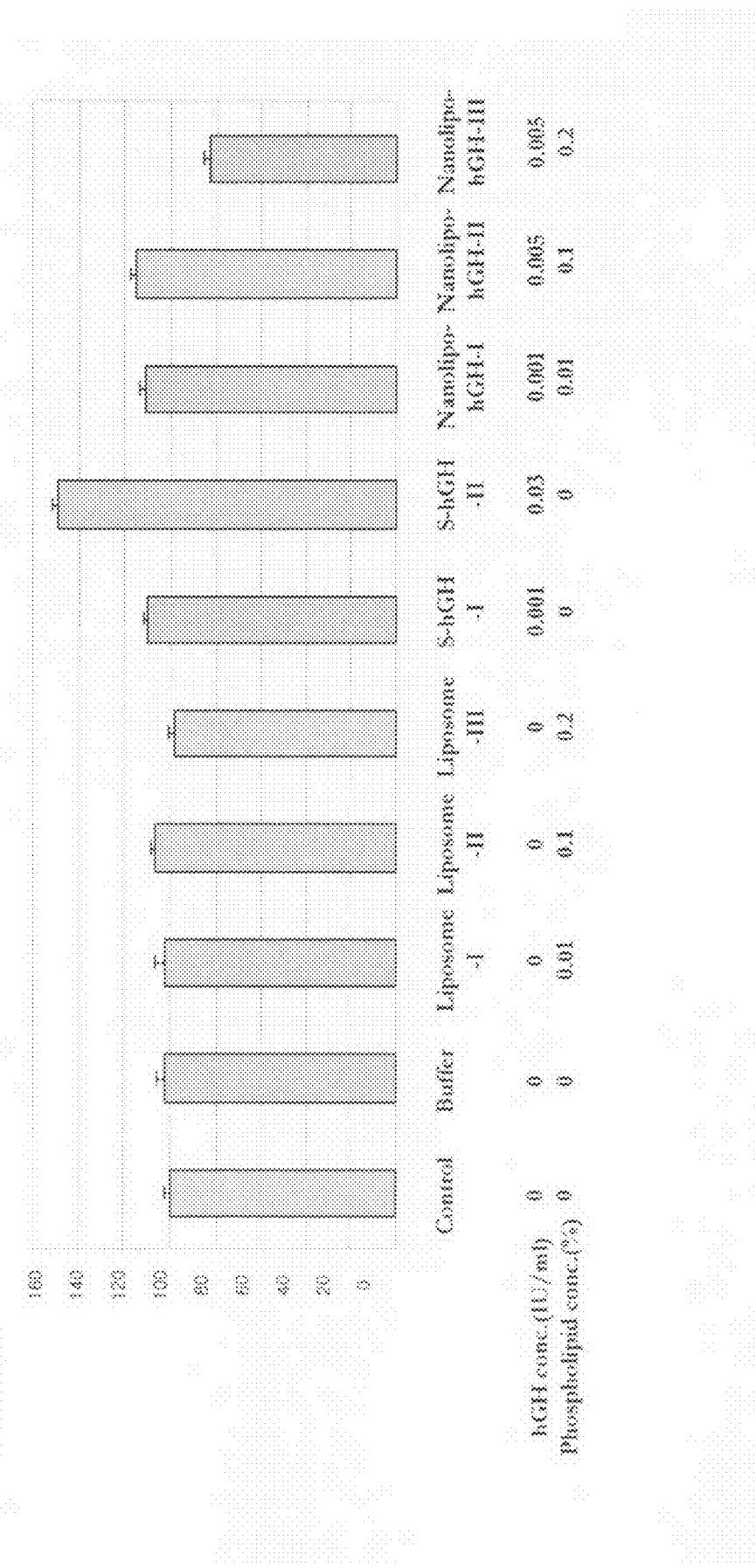
FIG. 7 is a graphic diagram showing safety test results for an hGH-containing liposome according to the present invention.

As can be seen in FIGS. 7A and 7B, the inventive hGH-containing nanoliposome had no effect the cell viability of HaCaT and HEF, indicating that it is a formulation very safe to a living body.

Example VII

Analysis for Proliferation of Nanoliposome Formulation Nanolipo-hGH in $Nb_2$ Cells To the well of a 96-well plate containing 50 µl of the $Nb_2$ noble rat lymphoma cell line (NIBSC ECACC #97041101) at a concentration of $1 \times 10^5$ cells/ml, S-hGH (standard human growth hormone, NIBSC code 98/574), a sample comprising a 1000-fold dilution of a pretreated solution (obtained by disrupting a liposome solution containing no human growth hormone with a sonicator and adding a solution (containing 50 mM Tris-Cl pH 8.0, 1 mM EDTA, 8 M urea, 2% Tween 20) thereto in the same volume as the sample and then pipetting the mixture) added S-hGH, or a sample comprising a 1000-fold dilution of the Nanolipo-hGH (N-hGH; formulation B prepared in Example I) subjected to a sample pretreatment process (comprising disrupting a liposome solution containing no human growth hormone with a sonicator and adding a solution (containing 50 mM Tris-Cl pH 8.0, 1 mM EDTA, 8 M urea, 2% Tween 20) thereto in the same volume as the sample and then pipetting the mixture), was added. Each of the samples was cultured in a 5% $CO_2$ incubator at 37° C. for 5 days, and the amount of the proliferated cells was measured using MTT. The mean absorbance of the group containing hGH was calculated as a value relative to the mean absorbance of the control group containing no hGH, taken as 100%.

Figure 8:
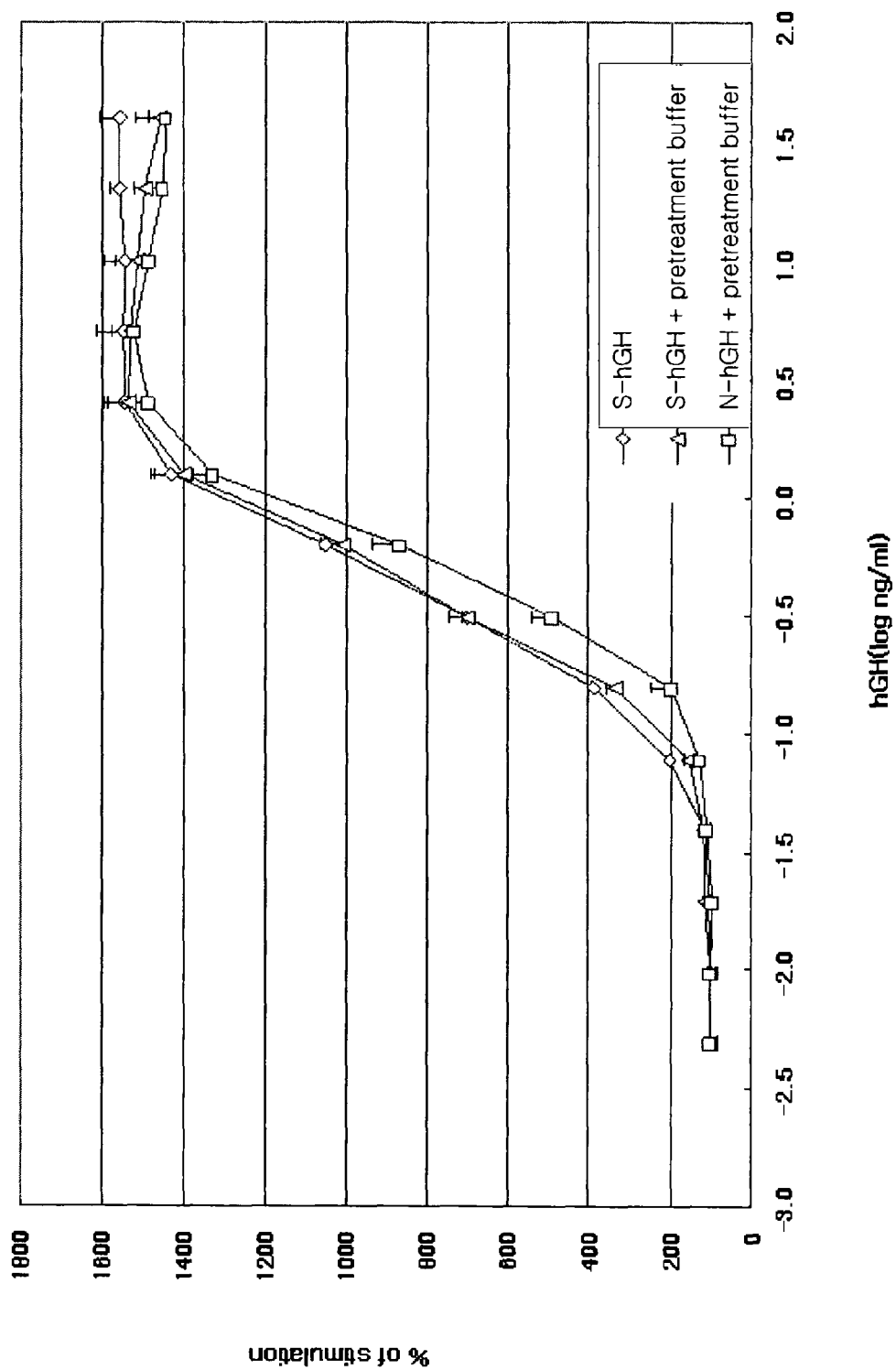
FIG. 8 shows analysis results for the activity of human growth hormone encapsulated in an hGH-encapsulating liposome according to the present invention.

As can be seen in FIG. 8, the human growth hormone encapsulated in the inventive Nanolipo-hGH maintained its original activity.

Example VIII

Analysis of Particle Size Distribution

Figure 9:
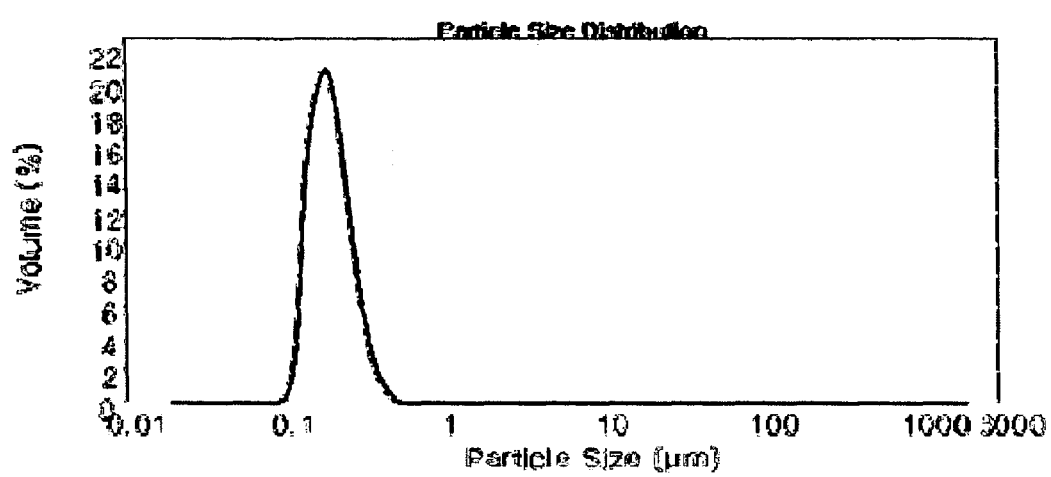
FIG. 9 shows analysis results for the particle size distribution of an hGH-encapsulated nanoliposome according to the present invention.

The Nanolipo-hGH of formulation B separated by gel permeation chromatography in the above Example was analyzed for particle size distribution at a refractive index of 1.52 using a particle size analyzer (Mastersizer 2000/Malvern Instruments Ltd.) (see FIG. 9). As can be seen in FIG. 9, the inventive Nanolipo-hGH showed the largest distribution at a particle size of 0.193 µm, indicating that the Nanolipo-hGH of formulation B is present in the nanometer size.

Example IX

Analysis of Wrinkle-Improving Effect 4-week-old nude mice (purchased from Korea Research Institute of Chemical Technology) were tested using the Nanolipo-hGH (N-hGH). An animal breeding chamber was kept at a temperature of 22±2° C. and a humidity of 55-60% in a 12-hr light/12-hr dark cycle, and the animals were permitted free access to solid feed (Central Lab. Animal Inc., Seoul, Korea) and water sterilized by irradiation and were acclimated for about 2 weeks. In order to induce wrinkles on the backside of these nude mice, 20 mJ of UVB was irradiated to the mice three times a week for 8 weeks. Then, to the UVB-irradiated back, each of a sample solution and a control solution were applied using a cosmetic brush for 8 weeks. Then, a wrinkle-improving effect was evaluated according to the Donald method (Hyun-Seok Kim et. al, *Mech. Ageing Dev.* (2005. 8.16 In press)).

Figure 10:
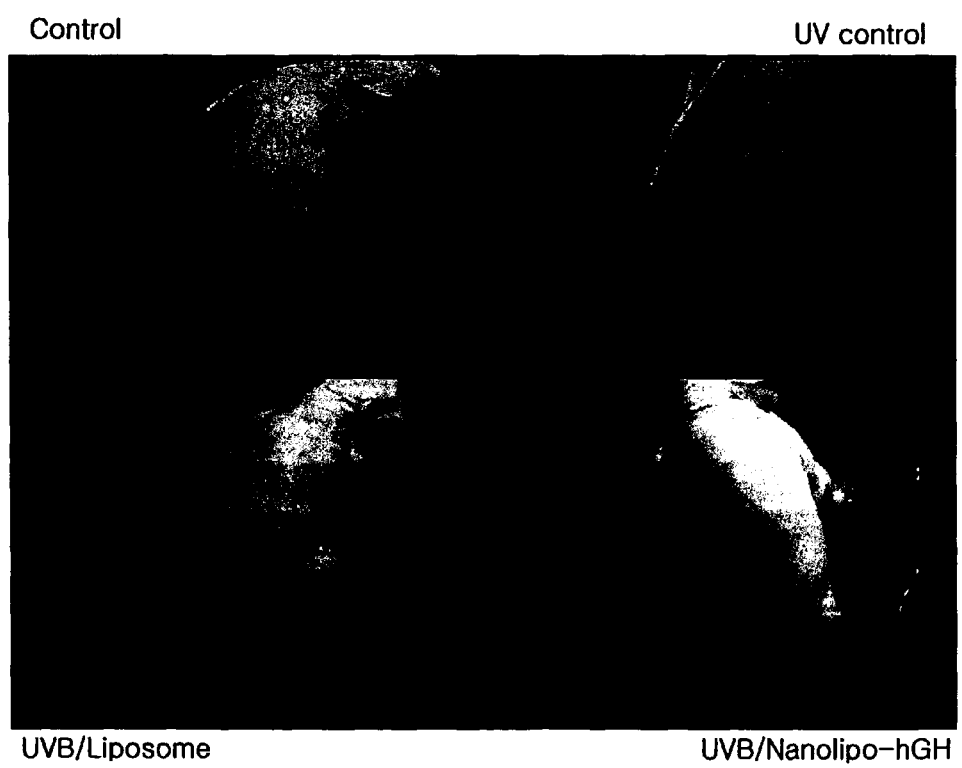
FIG. 10 shows test results for the wrinkle-reducing effect of the inventive hGH-encapsulated liposome on nude mice having UV-induced wrinkles.
Figure 11:
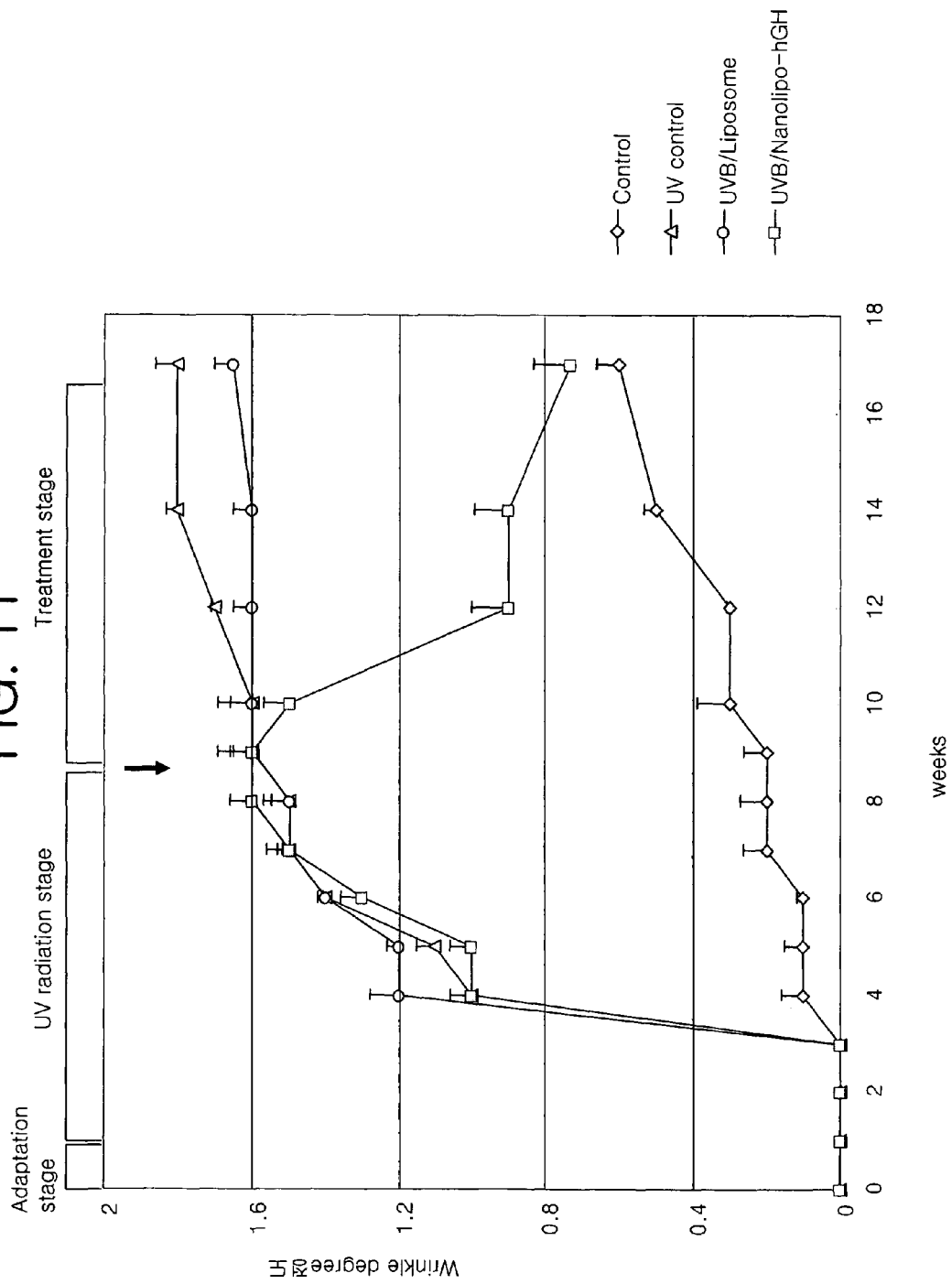
FIG. 11 is a graphic diagram showing the wrinkle-reducing effect of the inventive hGH-encapsulated nanoliposome.

The test results are shown in FIGS. 10 and 11. In FIG. 10, the control group (n=3) was not treated with anything, the UVB-control group (n=3) was treated with 20 mJ of UVB to induce only wrinkles, the liposome (n=3) was treated with 20 mJ of UVB to induce wrinkle and was treated with liposome, and the Nanolipo-hGH group (n=3) was treated with 20 mJ of UVB to induce wrinkles and treated with the inventive Nanolipo-hGH. As can be seen in FIGS. 10 and 11, the inventive Nanolipo-hGH had the effect of effectively removing the UV-induced wrinkles, which was clearly shown starting from 2 weeks after the topical application of the inventive Nanolipo-hGH.

Example X

Analysis of Acne Treatment Effect

The acne treatment effect of the inventive human growth hormone-containing liposome was examined in the following manner.

Sixty 15-40-year-old women were randomly divided into three groups, and then allowed to use each of the hGH-containing liposome formulation B of Example I (formulation 1), a comparative solution containing only liposome (formulation 2) and a comparative buffer solution (formulation 3) first after face washing two times (morning and evening) a day for 3 weeks. In addition, there was no particular limitation on usually used cosmetics. Then, the improvement of acne was evaluated based on the user's opinion according to the following criteria. The rest results are shown in Table 1 below. Evaluation criteria: +++ (had a very good improvement effect); ++ (had a significant improvement effect); + (had a slight improvement effect); ± (had no improvement effect, but not became worse); and − (became worse).

TABLE 1

| Period | Formulation 1 | Formulation 2 | Formulation 3 |
|---|---|---|---|
| $1^{st}$ week | + | ± | ± |
| $2^{nd}$ week | ++ | + | ± |
| $3^{rd}$ week | +++ | + | ± |

As can be seen in Table 1, the inventive formulation had a very good effect on the improvement of acne, which started to be clearly shown 2 weeks after the application of the formulation. Furthermore, the inventive composition did not substantially cause irritation to the skin, for example, erythema or itching.

Example XI

Analysis of Dark Spot Removal Effect

The dark spot removal effect of the inventive human growth hormone-containing liposome was tested in the following manner.

Sixty 40-60-year-old women were randomly divided into three groups, and then allowed to use each of the hGH-containing liposome formulation B of Example I (formulation 1), a comparative solution containing only liposome (formulation 2) and a comparative buffer solution (formulation 3) first after face washing two times (morning and evening) a day for 8 weeks. In addition, there was no particular limitation on usually used cosmetics. The improvement of dark spots was evaluated based on the user's opinion according to the following criteria. The test results are shown in Table 2 below. Evaluation criteria: +++ (had a very good improvement effect); ++ (had a significant improvement effect); + (had a slight improvement effect); ± (had no improvement effect, but not became worse); and − (became worse).

TABLE 2

| Period | Formulation 1 | Formulation 2 | Formulation 3 |
|---|---|---|---|
| $1^{st}$ week | ± | ± | ± |
| $2^{nd}$ week | ± | ± | ± |
| $3^{rd}$ week | + | ± | ± |
| $4^{th}$ week | + | ± | ± |
| $5^{th}$ week | ++ | + | ± |
| $6^{th}$ week | ++ | + | ± |
| $7^{th}$ week | ++ | + | ± |
| $8^{th}$ week | ++ | + | ± |

As can be seen in Table 2, the inventive formulation had a significantly excellent effect on the improvement of dark spots, which started to be clearly shown from about 3-5 weeks after the application of the formulation. Furthermore, the inventive composition did not substantially cause irritation to the skin, for example, erythema or itching.

Example XII

Analysis of Localization of Nanoliposome Formulation Nanolipo-hGH and Effect Thereof on Skin The abdominal region of a Sprague Dawley rat was divided into six zones (circles each having a radius of 1 cm) and treated with the following samples: 0.1% methyl-paraben buffer solution, 0.1% liposome, 0.001 U hGH, 0.0001 U hGH, 0.001 U Nanolipo-hGH, and 0.0001 U Nanolipo-hGH.

The animal was treated with each of the samples in an amount of 50 µl two times at 24-hour intervals seven times in total. At 24 hours after treatment with the last sample, tissue was extracted from the rat. The extracted tissue was sectioned to a thickness of 40 µm and treated with a polyclonal rabbit anti-human growth hormone primary antibody (DAKO, U.S.A.) and then with a biotin-conjugated anti-rabbit secondary antibody (VECTOR. VECTASTAIN ABC kit (RABBIT IgG), U.S.A.) at room temperature for 30 minutes. Next, the sectioned tissue was treated with a VECTASTAIN ABC reagent (VECTOR, U.S.A.) at room temperature for 30 minutes and subjected to a color development reaction with a DAB substrate (Diaminobenzidine, Sigma, USA). The sectioned tissue was dehydrated with 78% ethanol, 85% ethanol and 95% ethanol in order and then treated with xylene for 5 minutes. The tissue was fixed on a slide glass, and then the location of human growth hormone contained in Lipo-hGH was observed.

Figure 12A:
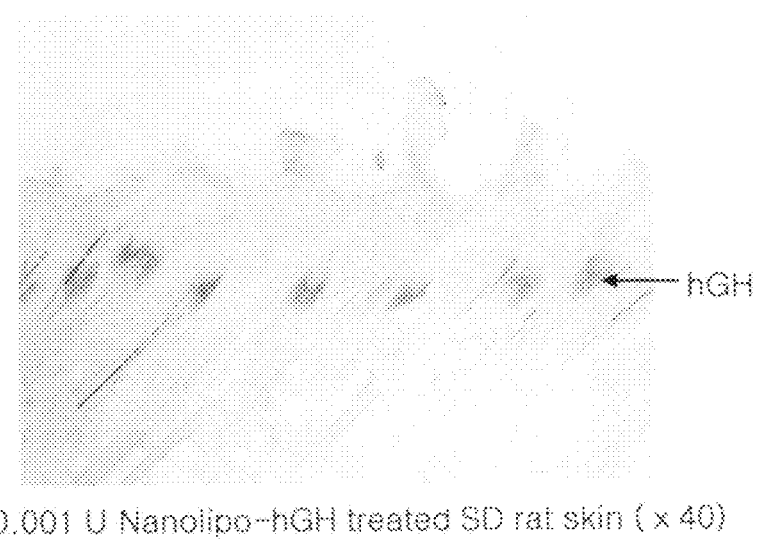
FIG. 12A is a photograph showing the localization of human growth hormone, which occurs when the inventive hGH-encapsulating nanoliposome is delivered to the skin through hair follicles in Sprague Dawley rats.

As can be seen in FIG. 12a, the human growth hormone encapsulated in the inventive Nanolipo-hGH or the rat growth hormone originally contained in the rat was found at locations considered as the bulge stem cells of hair follicles.

Figure 12B:
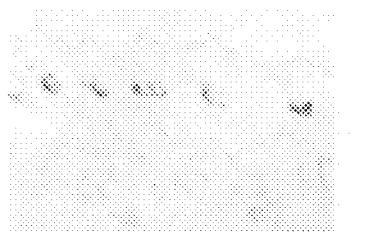
FIG. 12B is a photograph showing the effect of buffer on the dermal layer and hair follicles of the skin of Sprague Dawley rats.
Figure 12C:
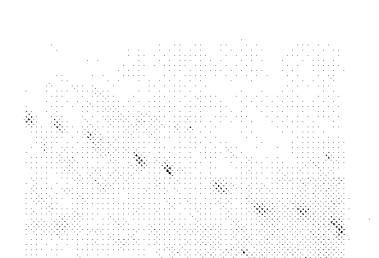
FIG. 12C is a photograph showing the effect of 0.001 unit hGH on the dermal layer and hair follicles of the skin of Sprague Dawley rats.
Figure 12D:
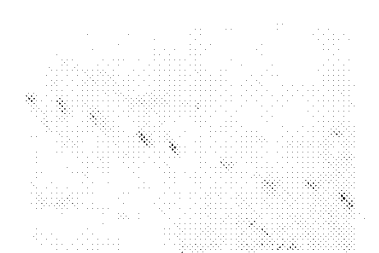
FIG. 12D is a photograph showing the effect of the inventive hGH-encapsulated nanoliposome on the dermal layer and hair follicles of the skin of Sprague Dawley rats.

Also, as can be seen in FIGS. 12B, 12C and 12D, the dermal layer of the rat skin applied with the inventive Nanolipo-hGH (containing 0.0001 U hGH) widened, and the number of hair follicles on the dermal layer increased. Furthermore, it can be found in FIGS. 12A to 12D that, even the hGH aqueous solution was applied to the skin, the hGH reached the location of bulge stem cells in hair follicles, and this finding was very surprising considering the technical level and common sense in the art. This result a possibility of achieving the improvement of skin conditions, even when not only hGH encapsulated in liposome, but also an hGH aqueous solution itself, are applied to the skin.

Example XIII

Analysis of Effect of Nanoliposome Formulation Nanolipo-hGH on Mouse Skin

The effect of the inventive nanoliposome formulation Nanolipo-hGH (prepared in Example I) on the skin of ICR mice was analyzed by H&E (Hematoxylin & Eosin) staining. For this purpose, after removing the hairs of the back of ICR mice, the back regions divided with respect to the vertebra were treated with a control group and the inventive Nanolipo-hGH at 4-hr intervals for 2 weeks: group 1 (n=3); untreated group 2 (n=3); a group (n=3) treated with liposome/0.1 U of the inventive Nanolipo-hGH; group 3 (n=3) treated with liposome/0.01 U of the inventive Nanolipo-hGH; group 4 (n=3) treated with liposome/0.001 U of the inventive Nanolipo-hGH. After 2 weeks of the treatment, tissues were extracted from the mice. The extracted tissues were made into paraffin blocks and sectioned to a thickness of 4 vm, and the sectioned tissues were placed on a slide glass. Then, the sections were deparaffined and treated with a hematoxylene solution at room temperature for 10 minutes and then with an eosin solution at room temperature for 1 minute. Next, the sections were dehydrated with 78% ethanol, 85% ethanol, 95% ethanol and 100% ethanol in order and then treated with xylene for 5 minutes. The tissues were immobilized, and then the stained tissues were observed under a microscope.

Figure 13A:
FIG. 13A is a photograph showing on the epidermis and dermis of the skin of ICR mice not treated.
Figure 13B:
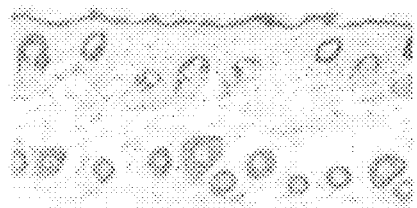
FIG. 13B is a photograph showing the effect of liposome on the epidermis and dermis of the skin of ICR mice.
Figure 13C:
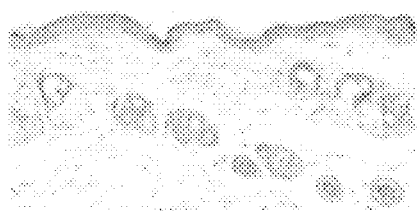
FIG. 13C is a photograph showing the effect of the inventive hGH-encapsulated nanoliposome on the epidermis and dermis of the skin of ICR mice.
Figure 13D:
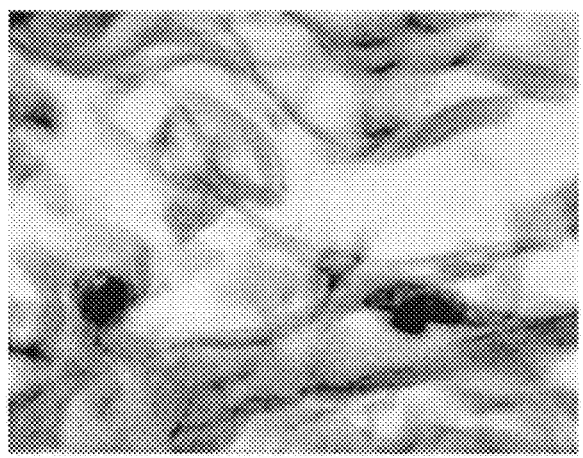
FIG. 13D is a photograph showing the connective tissue in the dermal layer of ICR mice not treated.
Figure 13E:
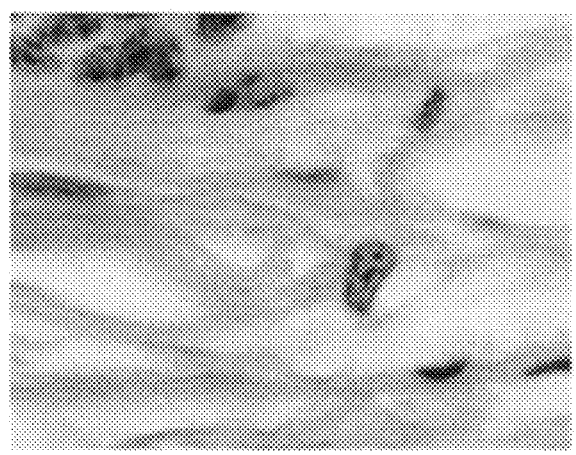
FIG. 13E is a photograph showing that the inventive hGH-encapsulated nanoliposome induces the remodeling of connective tissue in the dermal layer of ICR mice.

As can be seen in FIGS. 13A, 13B and 13C, the proliferation of cells in the epidermal layer of the skin treated with the inventive nanoliposome formulation Nanolipo-hGH was greatly increased, and the remodeling of connective tissues in the dermal layer occurred to form more compact connective tissues. FIGS. 13D, 13E and 13F are a photograph taken at 400× magnification and clearly show that the remodeling of connective tissues in the dermal layer occurred.

Example XIV

Analysis of Effect of Nanoliposome Formulation Nanolipo-hGH on Artificial Skin

Neoderm-ED™ (Tego Science, South Korea) was used to analyze the effect of the inventive nanoliposome formulation Nanolipo-hGH on artificial skin. Neoderm-ED™ is a human skin model for in vitro tests and consists of an epidermal and dermal matrix. Test groups were as follows: group 1 untreated; group 2 treated only with buffer solution; groups 3 and 4 treated with liposome; and groups 5 and 6 treated with 0.001 unit and 0.01 unit, respectively, of the inventive Nanolipo-hGH. Paraffin embedding and H&E staining were performed in the same manner as in the above Example. Finally, the stained tissues were observed under a microscope.

Figure 14A:
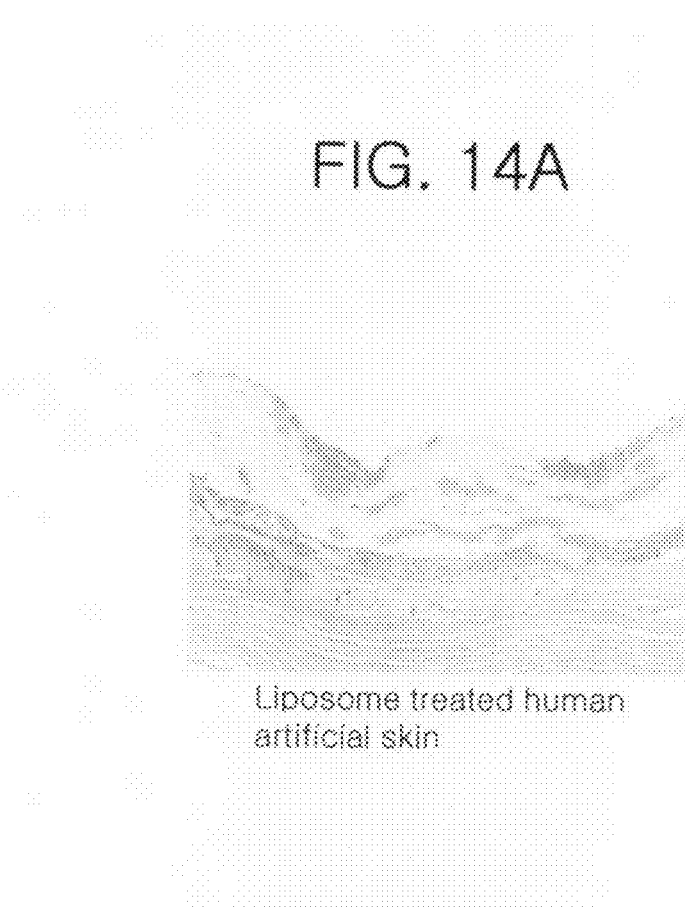
FIG. 14A is a photograph showing the effect of liposome on artificial human skin.
Figure 14B:
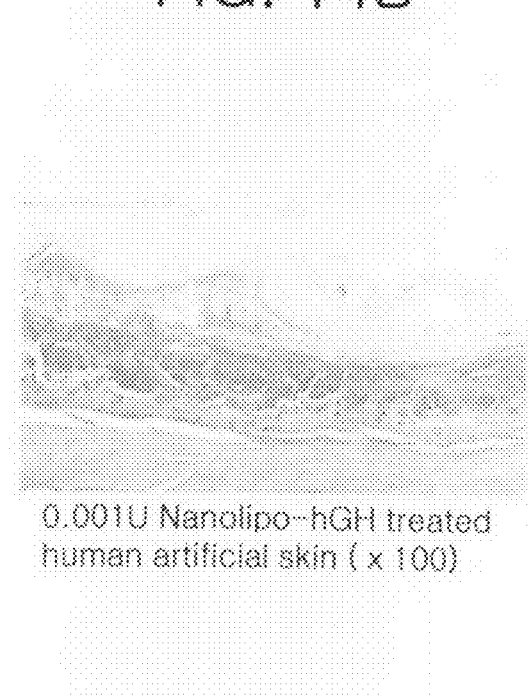
FIG. 14B is a photograph showing the effect of the inventive hGH-encapsulated nanoliposome on artificial human skin.

As can be seen in FIGS. 14A and 14B, the proliferation of cells in the keratinocyte layer of Neoderm-ED™ treated with the inventive nanoliposome formulation Nanolipo-hGH was actively made.

Example XV

Analysis of Hair Loss Prevention and Hair Growth Activities

The hair loss prevention and hair growth activities of the inventive Nanolipo-hGH were analyzed in the following manner. 8-week-old C57BL/6 mice (Jung Ang Lab Animal Inc., South Korea) in the telogen stage were anesthetized with ketamine and rompun, and the hairs of the back portions were removed with a depilatory. At 24 hours after the removal of the hairs, the mice were treated with 0.01 unit Nanolipo-hGH (containing 0.003 mg/ml hGH and 0.5% soybean lecithin) of formulation 2 prepared in Example I or liposome (containing 0.5% soybean lecithin): The treated animals were divided into groups 1 and 2 each consisting of three mice. Group 1 was treated with 150 µl of the formulation two times a day for 19 days, and group 2 was treated with 100 µl of the formulation two times a day for 19 days. In group 1, the left/right sides divided with respect to the vertebra were treated with the same or different substances. Mouse 1 was not treated with anything at the left/right sides, mouse 2 was untreated at the left side and treated with 0.01 unit Nanolipo-hGH at the right side, and mouse 3 was treated with liposome at the left side and treated with 0.01 unit Nanolipo-hGH at the right side. In group 2, each of the backs was treated at three divided portions of upper/middle/lower portions. Mouse 1 of group 2 was untreated at each of the upper/middle/lower portions, the mouse 2 was untreated at the upper portion, treated with liposome at the middle portion and treated with 0.01 unit Nanolipo-hGH at the lower portion, and mouse 3 was untreated at the upper portion, treated with liposome at the middle portion and treated with 0.01 unit Nanolipo-hGH at the lower portion.

At 3 hours after the final treatment, each of the mice was sacrificed, and tissues were collected from the sacrificed animals, and then fixed with 10% formalin (Yakuri, Japan) diluted in 1×PBS at room temperature. Following fixation, paraffin (Tyco Healthcare, U.S.A.) blocks were prepared and sectioned to a size of 10 µm. The sectioned paraffin blocks were incubated at 60° C. for 2 hours, cooled at room temperature and immersed in xylene for 10 minutes. This process comprising incubation, cooling and immersion was repeated three times so as to remove the surrounding paraffin. Then, the tissues were immersed and hydrated in each of 100%, 95%, 90%, 80% and 70% ethanol and distilled water, and then washed with flowing water. Next, the tissues were stained with a hematoxylin solution (Sigma, U.S.A.) for 10 minutes and washed with flowing water for 10 minutes. Then, the tissues were immersed in 1% HCl diluted in 70% ethanol and removed immediately after the immersion, and then washed with flowing water for 10 minutes. Thereafter, the tissues were treated with an eosin solution (Alpha Chem, Inc, U.K.) for 1 minute and then washed with flowing water for 10 minutes. Then, the tissues were dehydrated by sequential treatment with 70%, 80%, 90%, 95%, 100% ethanol and xylene. The tissues on a slide glass were fixed with a cover glass and observed under a microscope (×40).

Figure 15A:
FIG. 15A is a photograph showing the results of immunohistochemical analysis of non treated skin.
Figure 15B:
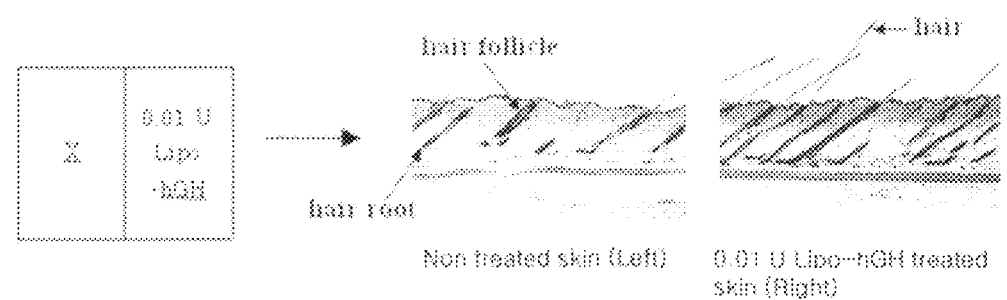
FIG. 15B is a photograph showing the results of immunohistochemical analysis conducted to examine the location of hGH delivered into hair follicles with the aid of the inventive hGH-encapsulated nanoliposome.

In FIGS. 15A and 15B showing test results for group 1, it can be seen that the number of hair follicles in the mice treated with the inventive Nanolipo-hGH was greatly increased. Also, the hair roots were generally located in the lower layer of the skin of the mice treated with the Nanolipo-hGH (corresponding to the late anagen stage or early catagen stage of the hair cycle), and were located in the upper layer of the skin in the untreated mouse (corresponding to the catagen stage of the hair cycle). These results suggest that the inventive Nanolipo-hGH delays the hair cycle.

Figure 15C:
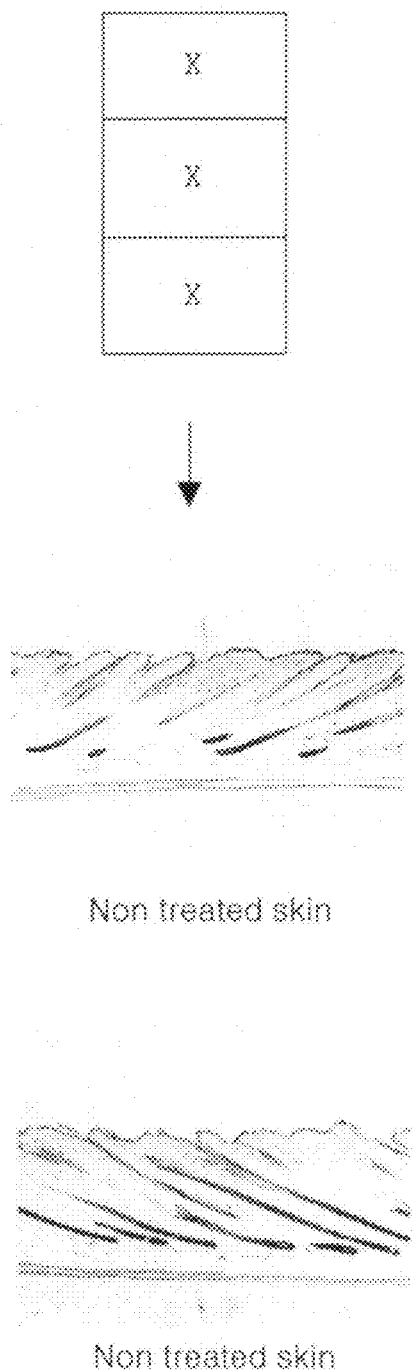
FIG. 15C is a photograph showing the results of immunohistochemical analysis of non treated skin.
Figure 15D:
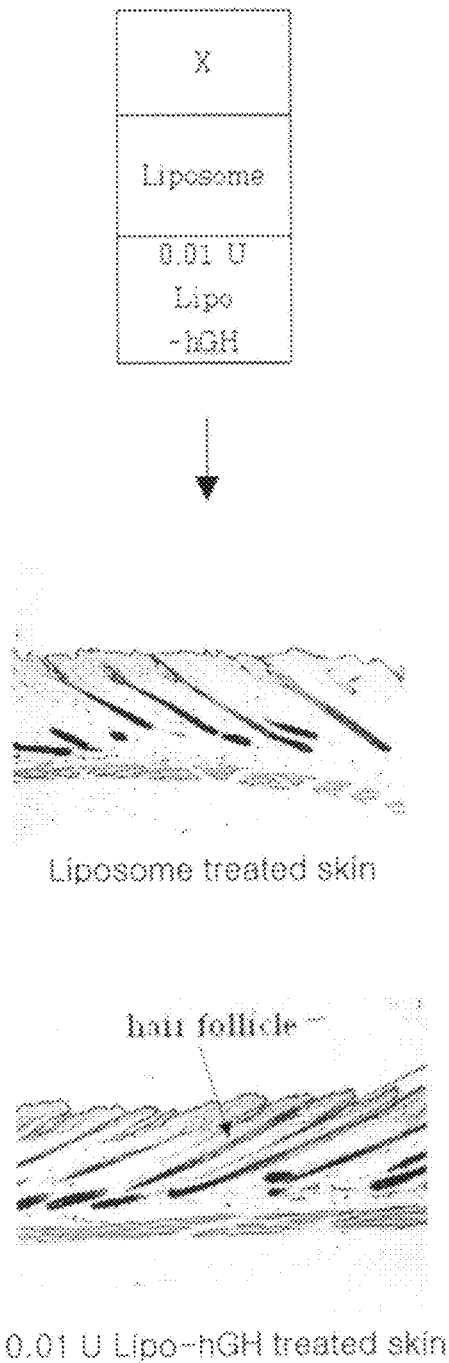
FIG. 15D is a photograph showing the results of immunohistochemical analysis conducted to examine the location of hGH delivered into hair follicles with the aid of the inventive hGH-encapsulated nanoliposome.
Figure 15E:
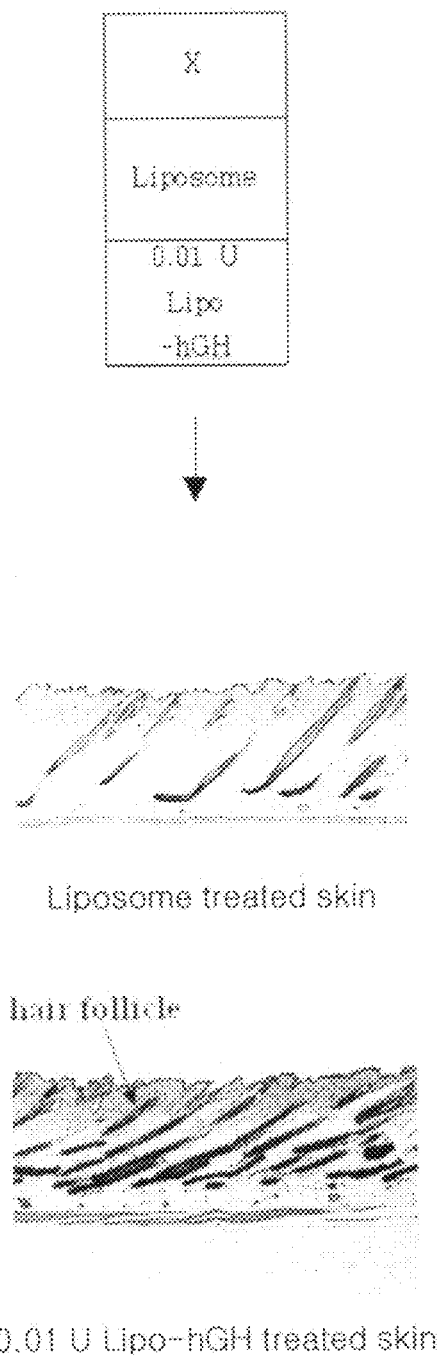
FIG. 15E is a photograph showing the results of immunohistochemical analysis conducted to examine the location of hGH delivered into hair follicles with the aid of the inventive hGH-encapsulated nanoliposome.

In FIGS. 15C to 15E showing test results for group 2, it can also be seen that the number of hair follicles in the mice treated with the inventive Nanolipo-hGH was greatly increased.

Accordingly, it can be found that, when the inventive Nanolipo-hGH is topically applied to the skin, it will exhibit excellent effects on hair loss prevention and hair growth stimulation.

Example XVI

Identification of hGH Delivered by Nanoliposome Formulation Nanolipo-hGH 8-week-old mice C57BL/6 (Jung Ang Lab Animal Inc., South Korea) in the telogen stage were anesthetized with ketamine (Yuhan Corp.) and rompun (Bayer Korea Ltd.), and the hairs of the back portions were removed with a depilatory. The divided portions of the back were treated with 150 µl of each of 0.1 U Nanolipo-hGH and 0.1 U hGH two times a day for 19 days. From 4 hours before collecting tissues, the portions were treated at 30-minute intervals. The collected tissues were fixed in 10% formalin solution, and paraffin blocks were prepared and sectioned to a size of 10 µm. The sections were treated with a polyclonal rabbit anti-human growth hormone primary antibody (DAKO, U.S.A.) for 12 hours and then with a Texas-Red fluorescence-conjugated anti-rabbit secondary antibody (VECTOR) at room temperature for 1 hour and 30 minutes. Then, a DAPI-containing mounting medium (VECTOR) was dropped, and the sections were covered with a cover glass and observed under a fluorescent microscope. From the test results, hGH spots stained red could be identified along the outer root sheath cells in the hair follicles of the skin treated with Nanolipo-hGH.

Example XVII

Examination of Effect on Proliferation of Skin Dermal Fibroblasts and Epidermal Keratinocytes Whether the inventive Nanolipo-hGH has the effects of activating the fibroblasts of the skin dermal layer and proliferating the keratinocytes in the epidermal layer was examined in the following manner. The hairs of the back of ICR mice (Jung Ang Lab Animal Inc., South Korea) were removed with a depilatory. Then, the back skin was treated with 0.025 unit Nanolipo-hGH (containing 0.0075 mg/ml hGH and 0.4% soybean lecithin) of formulation B prepared in Example I or liposome (containing 0.4% soybean lecithin) two times a day for 5 days. At 3 hours after the final treatment, the mice were sacrificed, from which tissues were then collected. The collected tissues were subjected to H&E staining in the same manner as in Example X, and the stained tissues were observed under a microscope (×200).

Figure 16A:
FIG. 16A is a photograph showing hair follicles of non treated mouse skin.
Figure 16B:
FIG. 16B is a photograph showing hair follicles of mouse skin treated with the inventive hGH-encapsulated nanoliposome.

As can be seen in FIGS. 16A and 16B, the effect of proliferating kerationcytes was shown in the epidermal layer of the skin applied with the inventive Nanolipo-hGH. Meanwhile, although the effect of proliferating keratinocytes was shown also by liposome, this proliferation effect was much lower than that in the group treated with Nanolipo-hGH. Also, the number and activity of fibroblasts in the dermal layer were significantly higher in the skin applied with Nanolipo-hGH than in the skin not applied with Nanolipo-hGH.

Accordingly, it can be found that the inventive Nanolipo-hGH can act to prevent hair loss and to stimulate hair growth, by activating and proliferating dermal fibroblasts and proliferating epidermal keratinocytes.

Having described specific examples of the present invention, it is to be understood that such examples are only preferred embodiments and should not be construed as limiting the scope of the invention. Therefore, the substantive scope of the invention may be determined by appended claims and their equivalents.

What is claimed is:

1. A method for improving skin conditions of a human, which comprises topically administering to the skin of human a composition comprising an effective amount of human growth hormone as an active ingredient, wherein the human growth hormone is encapsulated into a liposome, and wherein the skin condition is selected from the group consisting of wrinkles, dark spots, acne, poor skin elasticity, poor hair growth, skin aging and poor skin moisture;

wherein the composition is applied to a normal skin surface and the composition is not administered in direct contact with blood.

2. The method according to claim 1, wherein the liposome is a nanoliposome.

3. The method according to claim 2, wherein the nanoliposome has a particle size of 50-250 nm.

4. The method according to claim 2, wherein the nanoliposome has a small unilamellar vesicle structure.

5. The method according to claim 2, wherein the human growth hormone encapsulated into the nanoliposome has the activity of 90-100% of an unencapsulated human growth hormone.

6. The method according to claim 1, wherein the composition comprises a cosmetically acceptable carrier or a pharmaceutically acceptable carrier.

* * * * *

UNITED STATES PATENT AND TRADEMARK OFFICE
CERTIFICATE OF CORRECTION

| | |
|---|---|
| PATENT NO. | : 8,846,611 B2 |
| APPLICATION NO. | : 11/279555 |
| DATED | : September 30, 2014 |
| INVENTOR(S) | : Dahl Kyun Oh et al. |

Page 1 of 1

It is certified that error appears in the above-identified patent and that said Letters Patent is hereby corrected as shown below:

On the title page, item (75), the third inventor's name should read as follows:

--Kyun Young Lee--

Signed and Sealed this
Twelfth Day of July, 2016

Michelle K. Lee
*Director of the United States Patent and Trademark Office*